(12) United States Patent
Gebert et al.

(10) Patent No.: US 9,364,407 B2
(45) Date of Patent: *Jun. 14, 2016

(54) HAIR DYE AGENT COMPRISING AMINOPYRIMIDINE DERIVATIVES

(71) Applicant: Henkel AG & Co. KGaA, Duesseldorf (DE)

(72) Inventors: Antje Gebert, Duesseldorf (DE);
Helmut Giesa, Meerbusch (DE);
Annika Koenen, Grevenbroich (DE)

(73) Assignee: Henkel AG & Co. KGaA, Dusseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/680,166

(22) Filed: Apr. 7, 2015

(65) Prior Publication Data

US 2015/0209257 A1    Jul. 30, 2015

Related U.S. Application Data

(63) Continuation of application No. PCT/EP2013/070423, filed on Oct. 1, 2013.

(30) Foreign Application Priority Data

Oct. 10, 2012  (DE) .................. 10 2012 218 460

(51) Int. Cl.
| | | |
|---|---|---|
| *A61Q 5/10* | (2006.01) | |
| *A61K 8/49* | (2006.01) | |
| *A61K 8/34* | (2006.01) | |
| *A61K 8/41* | (2006.01) | |
| *C09B 62/20* | (2006.01) | |

(52) U.S. Cl.
CPC ............. *A61K 8/4953* (2013.01); *A61K 8/347* (2013.01); *A61K 8/415* (2013.01); *A61K 8/4926* (2013.01); *A61Q 5/10* (2013.01); *C09B 62/205* (2013.01)

(58) Field of Classification Search
CPC ....... A61Q 5/10; A61K 8/4953; A61K 8/415; A61K 8/347; A61K 8/4926; C09B 62/205
USPC .......................................................... 8/405
See application file for complete search history.

(56) References Cited

U.S. PATENT DOCUMENTS 4,046,503 A    9/1977 Kubersky

FOREIGN PATENT DOCUMENTS

WO    2006/029712 A1    3/2006
WO    WO 2006/029712    *    3/2006    ............... A61Q 5/10

OTHER PUBLICATIONS

STIC Search Report dated May 18, 2015.*
English translation (Sep. 22, 2015) of the Patent No. WO 2006/029712.*
PCT International Search Report (PCT/EP2013/070423) dated Apr. 2, 2014.

* cited by examiner

*Primary Examiner* — Eisa Elhilo
(74) *Attorney, Agent, or Firm* — P. Scott Smith

(57) ABSTRACT

The application relates to agents for dyeing keratin fibers. The agent can be present in a cosmetic carrier and includes at least one compound of formula (I) and/or a physiologically compatible salt of this compound,

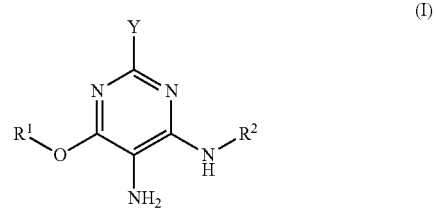

(I)

in which $R^1$ is a $C_1$-$C_4$ alkyl group, $R^2$ is a hydrogen atom, a $C_1$-$C_8$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group, a $C_1$-$C_6$ alkylamino group, a di-$C_1$-$C_6$ alkylamino group, a $C_1$-$C_6$ polyalkoxy group, a $C_1$-$C_6$ alkylamido-($C_1$-$C_6$) alkyl group, wherein the amide function can be substituted by one or two groups X, or is an aryl group, Y is an $NH_2$ or an OH group, at least one coupler component selected from 3-amino-2-methylamino-6-methoxypyridine, 3-amino-6-methylphenol, 3-amino-2-hydroxypyridine, 1,3-bis-(2,4-diaminophenoxy)propane, 2,7-dihydroxynaphthalene, 2-methylresorcinol, 2,5-dimethylresorcinol, 4-chlororesorcinol, 3-aminophenol, 2-amino-3-hydroxypyridine, 2-chloro-6-methyl-3-aminophenol, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 1-methoxy-2-amino-4-beta-hydroxy-ethylaminobenzene (Lehmann's blue), 2,4-diaminophenoxyethanol, 5-amino-4-chloro-o-cresol, 2,4-dichloro-m-aminophenol, 2,6-dihydroxy-3,4-dimethylpyridine and/or a physiologically compatible salt of these compounds.

9 Claims, No Drawings

HAIR DYE AGENT COMPRISING AMINOPYRIMIDINE DERIVATIVES

FIELD OF THE INVENTION

The present invention generally relates to an agent for changing the color of keratin-containing fibers, particularly human hair which comprises certain substituted aminopyrimidine derivatives in combination with certain coupler components.

The invention further relates to the use of the developer-coupling combination in dyes for improving the dyeing results.

BACKGROUND OF THE INVENTION

Modifying the shape and color of hair represents an important area of modern cosmetics. The consumer resorts to color-changing agents for fashionable hair style color schemes or for concealing gray or white hair with fashionable or natural color tints.

For the provision of color-changing cosmetic agents, especially for the skin or keratin-containing fibers such as for example human hair, the person skilled in the art is aware of diverse systems according to the requirements of the dyeing or color modification.

The so-called oxidation dyes are used for long-lasting, intensive colorations with corresponding authentic characteristics. Such dyes usually comprise oxidation dye precursors, the "developer components" and "coupler components". Under the influence of oxidizing agents or from atmospheric oxygen, the developer components form the actual colorants among each other or by coupling with one or more coupler components. The oxidation dyes are distinguished by intensive, outstanding, long-lasting coloration results. However, for colorations with a natural appearance, a mixture of a large number of oxidation dye precursors can be employed; in many cases, further substantive dyes are used for nuancing.

In spite of their advantageous coloration properties, oxidative hair dyeing agents often present disadvantages for the user, such that there is a constant need for further development of oxidation dye precursors.

In the search for oxidation dye precursors with a good tolerability profile, many compounds have been studied but they frequently suffer from application related problems, especially the lack of gray coverage capability. Moreover, in spite of the already highly developed dyeing systems, there still exists the need for dyeing systems that achieve excellent luminance and intensity of the colorations, and that at the same time, however, provide very good durability, very good fastness and an excellent homogeneity.

In particular, there is a need for improvement in the red coloration segment.

Many known dyeing systems, with which red color nuances can be obtained, provide inadequate wash fastness and insufficient leveling power.

In the published application DE 2516117, triaminoalkoxypyrimidine derivatives are proposed as toxicologically and dermatologically harmless developer components in oxidative hair dyes.

However, it was found that the obtained color nuances disclosed in DE 2516117 are not sufficiently numerous for today's requirements (particularly in the red tints). In addition, some of the coupler components cited in the abovementioned published application are suspected of being sensitizing and/or not toxicologically harmless.

Consequently, the object of the present invention is to reduce the abovementioned disadvantages of oxidative hair dyes. The dyes should produce intensive colorations with vivid colors and with a good resistance towards external influences, in particular with good fastness to light and to washing; also the colorations should suffer neither discoloration nor color shifts even after repeated shampooing of the hair. Furthermore, the dyeing should be as unselective as possible, i.e. achieve colorations that are as uniform and homogeneous as possible on differently pre-treated hair. Moreover, the dyes should have a toxicologically advantageous profile.

Another object of the invention is to find suitable toxicologically and dermatologically harmless coupler components for triaminoalkoxypyrimidine derivatives, with which a great number of color nuances—particularly red color nuances—can be obtained, and which exhibit excellent wash fastness and a particularly good leveling power. Finally, it is desirable to achieve as many nuances as possible of the individual color tints.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for dyeing keratinic fibers, in particular human hair, characterized in that said agent comprises in a cosmetic carrier: at least one compound of Formula (I) and/or a physiologically acceptable salt of said compound,

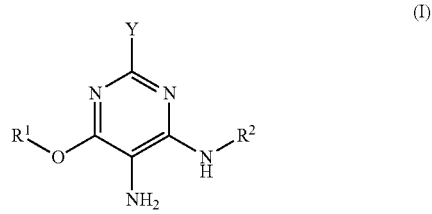

(I)

in which $R^1$ stands for a $C_1$-$C_4$ alkyl group, $R^2$ stands for a hydrogen atom, a $C_1$-$C_8$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group, a $C_1$-$C_6$ alkylamino group, a di-$C_1$-$C_6$ alkylamino group a $C_1$-$C_6$ polyalkoxy group, a $C_1$-$C_6$ alkylamido-($C_1$-$C_6$) alkyl group, wherein the amide function can be substituted with one or two X groups, or stands for an aryl group, Y stands for an $NH_2$ group or an OH group; and at least one coupler component, selected from the group consisting of 3-amino-2-methylamino-6-methoxypyridine, 3-amino-6-methylphenol, 3-amino-2-hydroxypyridine, 1,3-bis-(2,4-diaminophenoxy)propane, 2,7-dihydroxynaphthalene, 2-methylresorcinol, 2,5-dimethylresorcinol, 4-chlororesorcinol, 3-aminophenol, 2-amino-3-hydroxypyridine, 2-chloro-6-methyl-3-aminophenol, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 1-methoxy-2-amino-4-beta-hydroxyethylaminobenzene (Lehmann's blue), 2,4-diaminophenoxyethanol, 5-amino-4-chloro-o-cresol, 2,4- dichloro-m-aminophenol, 2,6-dihydroxy-3,4-dimethylpyridine and/or a physiologically acceptable salt of these compounds.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been found that the combination of certain alkoxylated aminopyrimidine derivatives together with certain coupler components as the oxidation dye precursors is outstandingly suitable for dyeing keratin-containing fibers. Colorations with good fastness, high color intensity and outstanding luster as well as excellent levelling power are achieved.

Accordingly, a first subject matter of the present invention is an agent for dyeing keratinic fibers, in particular human hair, characterized in that it comprises in a cosmetic carrier
a) at least one compound of Formula (I) and/or a physiologically acceptable salt of said compound,

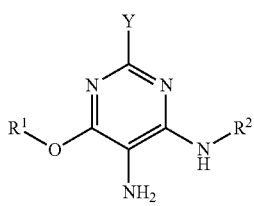

(I)

in which
$R^1$ stands for a $C_1$-$C_4$ alkyl group,
$R^2$ stands for a hydrogen atom, a $C_1$-$C_8$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group, a $C_1$-$C_6$ alkylamino group, a di-$C_1$-$C_6$ alkylamino group a $C_1$-$C_6$ polyalkoxy group, a $C_1$-$C_6$ alkylamido-($C_1$-$C_6$) alkyl group, wherein the amide function can be substituted with one or two X groups, or an aryl group, and
Y stands for an $NH_2$ group or an OH group, and
b) at least one coupler component, selected from the group consisting of 3-amino-2-methylamino-6-methoxypyridine, 3-amino-6-methylphenol, 3-amino-2-hydroxypyridine, 1,3-bis-(2,4-diaminophenoxy)propane, 2,7-dihydroxynaphthalene, 2-methylresorcinol, 2,5-dimethylresorcinol, 4-chlororesorcinol, 3-aminophenol, 2-amino-3-hydroxypyridine, 2-chloro-6-methyl-3-aminophenol, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 1-methoxy-2-amino-4-beta-hydroxy-ethylaminobenzene (Lehmann's blue), 2,4-diaminophenoxyethanol, 5-amino-4-chloro-o-cresol, 2,4-dichloro-m-aminophenol, 2,6-dihydroxy-3,4-dimethylpyridine and/or a physiologically acceptable salt of these compounds.

Keratinic fibers are understood to mean wool, furs, feathers and especially human hair. However, the dyes according to the invention can, in principle, also be used for dyeing other natural fibers, such as e.g. cotton, jute, sisal, linen or silk, modified natural fibers, such as e.g. cellulose regenerate, nitrocellulose, alkyl cellulose or hydroxyalkyl cellulose or acetyl cellulose.

The inventive agents comprise the components a) and b) in a cosmetic carrier, preferably in a suitable aqueous, alcoholic or aqueous alcoholic carrier. For the purposes of dyeing hair, such carriers are, for example, creams, emulsions, gels or also surfactant-containing foaming solutions, such as, for example, shampoos, foam aerosols, foam formulations or other preparations that are suitable for use on the hair. However, it is also conceivable to integrate the compounds of Formula (I) into a powdered or also tablet-shaped formulation.

In the context of the present invention, aqueous-alcoholic solutions are understood as meaning aqueous solutions comprising 3 to 70 wt % of a $C_1$-$C_4$ alcohol, in particular, ethanol or isopropanol. The agents according to the invention can additionally comprise further organic solvents, such as, for example, methoxybutanol, benzyl alcohol, ethyl diglycol or 1,2-propylene glycol. Preference here is given to all water-soluble organic solvents.

Examples of a $C_1$-$C_8$ alkyl group are the groups methyl, ethyl, propyl, isopropyl, n-butyl, s-butyl and t-butyl, n-pentyl, i-pentyl, i-hexyl, n-hexyl, i-heptyl, n-heptyl, i-octyl and n-octyl. Examples of a $C_2$-$C_6$ alkenyl group are vinyl, allyl, but-2-enyl, but-3-enyl and isobutenyl; preferred $C_2$-$C_6$ alkenyl residues are vinyl and allyl. Preferred examples of a $C_1$-$C_6$ hydroxyalkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Inventively preferred $C_1$-$C_6$ alkoxy groups are the methoxy, ethoxy or the propoxy group. Examples of a $C_2$-$C_6$ polyhydroxyalkyl group are the 2,3-dihydroxypropyl group, 3,4-dihydroxybutyl group and the 2,4-dihydroxybutyl group. The methylamino, the ethylamino and the propylamino groups may be cited as examples of a $C_1$-$C_6$ alkylamino group. The dimethylamino, the diethylamino and the dipropylamino groups are examples of a di-$C_1$-$C_6$ alkylamino group. Exemplary $C_1$-$C_6$ alkylamido-$C_1$-$C_6$ alkyl groups are the N-methyl-2-acetamide group, N,N-dimethyl-2-acetamide group, the N-ethyl-2-acetamide group, the N,N-diethyl-2-acetamide group, the N-methyl-3-propanamide group, the N,N-dimethyl-3-propanamide group, the N-ethyl-3-propanamide group and the N,N-diethyl-3-propanamide group. Inventively preferred examples of polyalkoxy groups are the (methoxymethoxy)methoxy group, the 2-(2-methoxyethoxy)ethoxy group, the 3-(3-methoxypropoxy)propoxy group, the (ethoxymethoxy)methoxy group, the 2-(2-ethoxyethoxy)ethoxy group and the 3-(3-ethoxypropoxy)propoxy group. Preferred examples of aryl groups are phenyl, toluyl and benzyl.

In the course of the work that led to this invention it was found that it is advantageous if dyes comprise at least one compound of the Formula (I), in which the $R^1$ residue stands for a methoxy, ethoxy, propoxy, 2-methylpropoxy, 3-methylbutoxy or a 2-methylbutoxy group, and the $R^2$ residue stands for a hydrogen atom, a $C_1$-$C_8$ alkyl group, an aryl group, a $C_1$-$C_6$ hydroxyalkyl group or a $C_1$-$C_6$ alkylamino group.

Particularly preferably, the $R^1$ residue in compounds according to Formula (I) stands for a methoxy, a 2-methylpropoxy or a 3-methylbutoxy group, and the $R^2$ residue stands for a hydrogen atom, a $C_1$-$C_8$ alkyl group or an aryl group.

If Y stands for an $NH_2$ group, then this is likewise particularly favourable for solving the problem according to the invention and is therefore preferred.

In a particularly preferred embodiment, the compounds according to Formula (I) are derivatives of 6-hydroxytriaminopyrimidine and are therefore amino compounds. The known acid addition salts can be prepared from these in the usual manner. All statements in this document and consequently the claimed extent of protection therefore relate both to the compounds present in free form as well as to their physiologically acceptable salts of organic or mineral acids. Examples of such salts are the hydrochlorides, the hydrobromides, the sulfates, the phosphates, the acetates, the propionates, the citrates and the lactates. In this regard, the hydrochlorides and the sulfates are particularly preferred. The monohydrochlorides, the dihydrochlorides and the trihydrochlorides are inventively quite particularly preferred.

A preferred embodiment of the first subject matter of the invention is therefore characterized in that the agent comprises at least one compound according to Formula (I) which is selected from

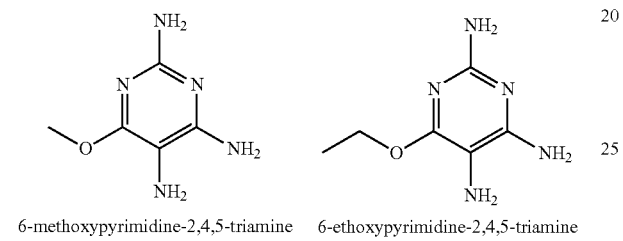

6-methoxypyrimidine-2,4,5-triamine    6-ethoxypyrimidine-2,4,5-triamine

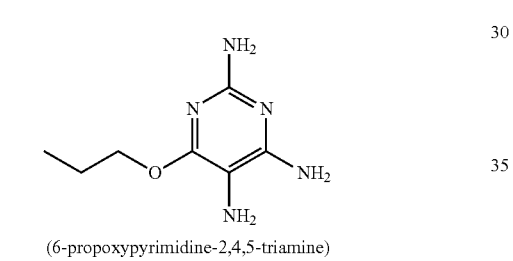

(6-propoxypyrimidine-2,4,5-triamine)

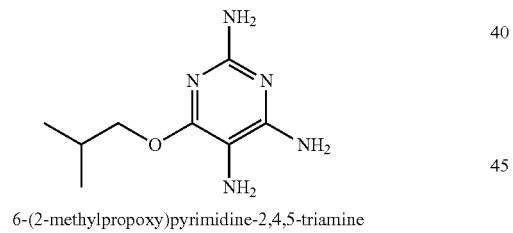

6-(2-methylpropoxy)pyrimidine-2,4,5-triamine

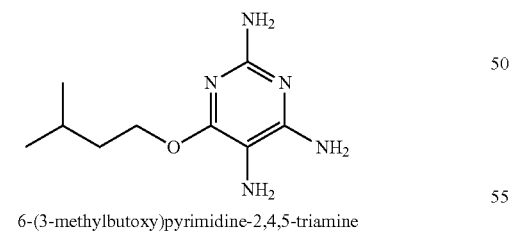

6-(3-methylbutoxy)pyrimidine-2,4,5-triamine

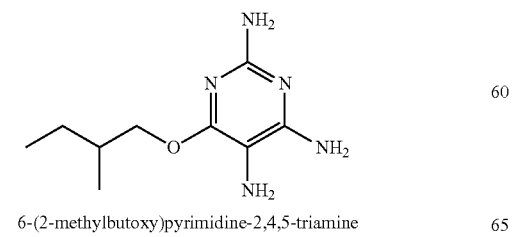

6-(2-methylbutoxy)pyrimidine-2,4,5-triamine

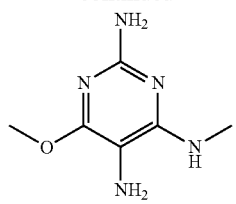

6-methoxy-$N^4$-methylpyrimidine-2,4,5-triamine

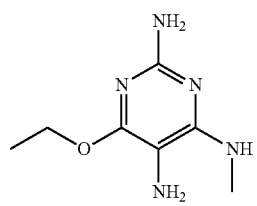

6-ethoxy-$N^4$-methylpyrimidine-2,4,5-triamine

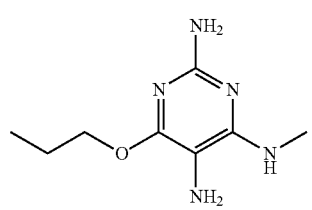

6-propoxy-$N^4$-methylpyrimidine-2,4,5-triamine

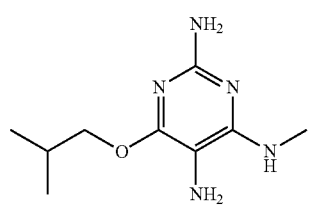

6-isobutoxy-$N^4$-methylpyrimidine-2,4,5-triamine

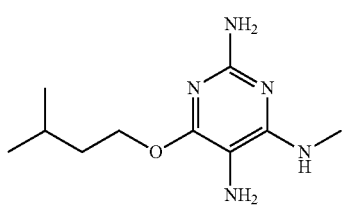

6-(3-methylbutoxy)-$N^4$-methylpyrimidine-2,4,5-triamine

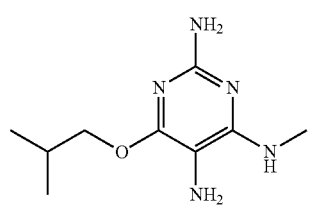

6-(2-methylbutoxy)-$N^4$-methylpyrimidine triamine

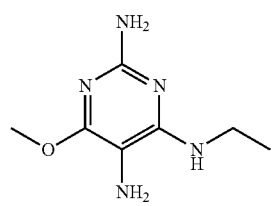

6-methoxy-$N^4$-ethylpyrimidine-2,4,5-triamine

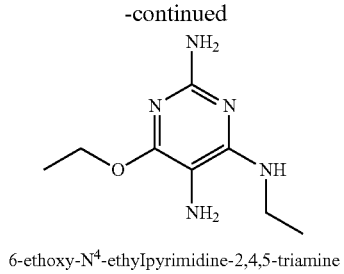
6-ethoxy-$N^4$-ethylpyrimidine-2,4,5-triamine

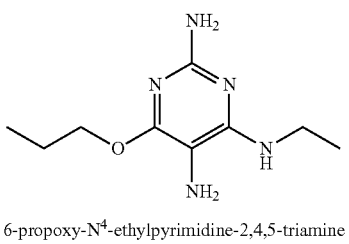
6-propoxy-$N^4$-ethylpyrimidine-2,4,5-triamine

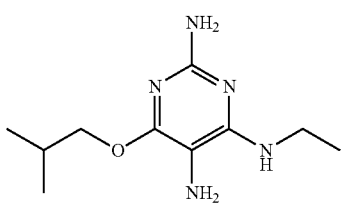
6-isobutoxy-$N^4$-ethylpyrimidine-2,4,5-triamine

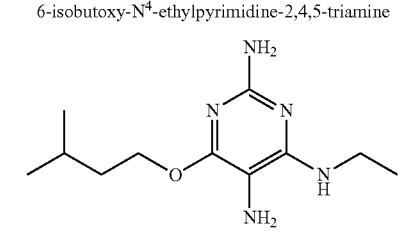
6-(3-methylbutoxy)-$N^4$-ethylpyrimidine-2,4,5-triamine

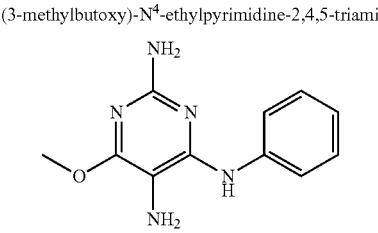
6-methoxy-$N^4$-phenylpyrimidine-2,4,5-triamine

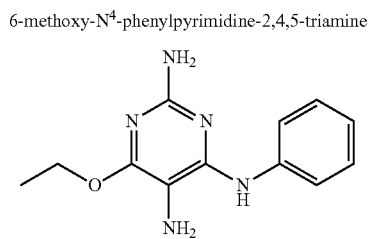
6-ethoxy-$N^4$-phenylpyrimidine-2,4,5-triamine

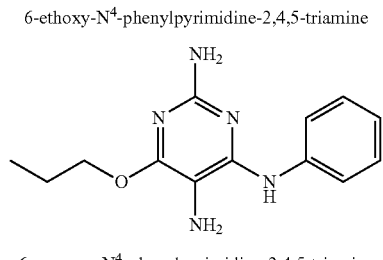
6-propoxy-$N^4$-phenylpyrimidine-2,4,5-triamine

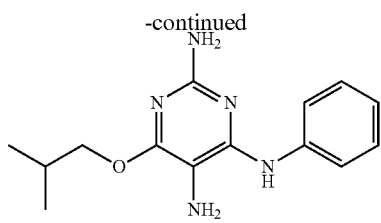
6-isobutoxy-$N^4$-phenylpyrimidine-2,4,5-triamine

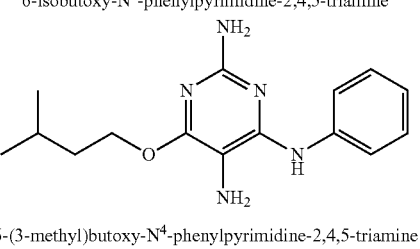
6-(3-methyl)butoxy-$N^4$-phenylpyrimidine-2,4,5-triamine

Within this preferred embodiment of the first subject matter of the invention, it is particularly preferred if the compound according to Formula (I) is 6-methoxy-2,4,5-pyrimidinetriamine, 6-(2-methylpropoxy)-2,4,5-pyrimidinetriamine, 6-(3-methylbutoxy)-2,4,5-pyrimidinetriamine, 6-methoxy-4-N-methylpyrimidine-2,4-diamine and/or a physiologically acceptable salt of these compounds.

Particularly fine colorations—particularly in the red and in the blue region—can be achieved if at least one of the compounds 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxy-ethylaminobenzene (Lehmann's blue) and/or a physiologically acceptable salt of these compounds as the coupling component b) is combined with at least one of the previously mentioned aminopyrimidine compounds.

In another particularly preferred embodiment, the coupler component b) is therefore selected from 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxy-ethylaminobenzene (Lehmann's blue) and/or from a physiologically acceptable salt of these compounds.

Inventively preferred agents are characterized in that they comprise the compounds of the Formula (I) and/or their physiologically acceptable salts in a quantity by weight of 0.001 to 5 wt %, preferably 0.025 to 2.5 wt %, particularly preferably 0.05 to 2.0 wt % and in particular 0.1 to 1.5 wt %, based on the total weight of the ready for use agent.

Similarly inventively preferred agents according to the invention are characterized in that they comprise the at least one coupler component b) and/or their physiologically acceptable salt in a quantity by weight of 0.001 to 5.0 wt %, more preferably 0.025 to 2.5 wt %, particularly preferably 0.05 to 2.0 wt % and in particular 0.1 to 1.5 wt %, each based on the total weight of the ready for use agent.

The following combinations a) and b) are particularly preferred:

6-methoxy-2,4,5-pyrimidinetriamine and one or more compounds, selected from 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxyethylaminobenzene (Lehmann's blue).

6-(2-methylpropoxy)-2,4,5-pyrimidinetriamine and one or more compounds, selected from 3-amino-2-methylamino-6- methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxyethylaminobenzene (Lehmann's blue).

6-(3-methylbutoxy)-2,4,5-pyrimidinetriamine and one or more compounds, selected from 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxyethylaminobenzene (Lehmann's blue).

6-methoxy-4-N-methylpyrimidine-2,4-diamine and one or more compounds, selected from 3-amino-2-methylamino-6-methoxypyridine, 3-amino-2-hydroxypyridine, 1,3-bis-(2, 4-diaminophenoxy)propane, 2,7-dihydroxynaphthalene, 2-methylresorcinol, 1-methoxy-2-amino-4-β-hydroxyethylaminobenzene (Lehmann's blue).

The combination of 6-methoxy-2,4,5-pyrimidinetriamine with one or more compounds, selected from 1,3-bis-(2,4-diaminophenoxy)propane, 2,7-dihydroxynaphthalene, 2-methylresorcinol is particularly preferred.

In the abovementioned combinations of oxidation dye precursors it can be likewise inventively advantageous to add a physiologically acceptable salt of these compounds instead of the uncharged compound.

In order to achieve a balanced and subtle development of nuances, it is inventively advantageous for additional chromophoric components to be comprised in the agent according to the invention.

It can therefore be inventively preferred for the agent to comprise at least one additional chromophoric component that is selected from further oxidation dye precursors of the developer type and/or substantive dyes.

In addition to the oxidation dye precursors of the developer type according to Formula (I), the inventive agents can additionally comprise at least one further developer component.

Preferred additional developer components are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as the physiologically acceptable salts of these compounds. Particularly preferred additional developer components in this regard are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole as well as their physiologically acceptable salts.

The additional developer components are preferably used in an amount of 0.0001 to 10 wt %, preferably 0.001 to 5 wt %, in each case based on the ready-for-use agent.

The inventive agents can further comprise at least one substantive dye. These are dyes that are directly absorbed onto the hair and do not require any oxidative process to develop the color. Substantive dyes are usually nitrophenylenediamines, nitroaminophenols, azo dyes, anthraquinones or indophenols.

The substantive dyes are preferably employed in quantities of 0.001 to 20 wt %, in particular 0.05 to 5 wt %, each based on the total end-use preparation. The total amount of substantive dyes is preferably 3 wt % at most.

Substantive dyes can be subdivided into anionic, cationic and non-ionic substantive dyes which are selected and employed by the person skilled in the art based on the requirements of the carrier.

Preferred anionic substantive dyestuffs are known compounds with the international designations or trade names bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyestuffs are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 as well as Yellow 87, Basic Orange 31 and Basic Red 51.

Non-ionic nitro and quinone dyes and neutral azo dyes are particularly suitable as non-ionic substantive dyes. Preferred non-ionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-Amino-4-nitrophenol, 1,4-bis-(2-hydroxyethyl)-amino-2-nitrobenzene, 3-nitro-4-(2-hydroxyethyl)aminophenol, 2-(2-Hydroxyethyl)amino-4,6-dinitrophenol, 4-[(2-Hydroxyethyl)amino]-3-nitro-1-methylbenzene, 1-amino-4-(2-hydroxyethyl)amino-5-chloro-2-nitrobenzene, 4-Amino-3-nitrophenol, 1-(2'-ureidoethyl)amino-4-nitrobenzene, 2-[(4-Amino-2-nitrophenyl)amino]-benzoic acid, 6-nitro-1,2,3,4-tetrahydroquinoxaline, 2-hydroxy-1,4-naphthoquinone, picramic acid and its salts, 2-Amino-6-chloro-4-nitrophenol, 4-ethylamino-3-nitrobenzoic acid and 2-chloro-6-ethylamino-4-nitrophenol.

In addition to the compound according to Formula (I) the inventive agents can also comprise dyes that are analogous to nature. Preparations according to the invention which comprise precursors of nature-analogous dyes are preferably used as the atmospherically oxidative colorant. In this embodiment, an additional oxidizing agent is consequently not added to the cited compositions.

The dye precursors of nature-analogous dyes are each preferably employed in a quantity of 0.001 to 5 wt %, based on the total end-use preparation. Derivatives of 5,6-dihydroxyindoline, in particular 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline as well as 5,6-dihydroxyindoline-2-carboxylic acid, as well as other derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, as well as physiologically acceptable salts of the abovementioned compounds are suitable as particularly good precursors of nature-analogous hair dyes.

In the case of the oxidative dyeing, the color development can in principle occur with atmospheric oxygen. However, it is preferred to use a chemical oxidizing agent, particularly when a lightening effect on human hair is desired in addition to the dyeing. This lightening effect may be desired independently of the dyeing method. Persulfates, peroxydisulfates, chlorites, hypochlorites and particularly hydrogen peroxide or and/or one of its solid addition products on organic or inorganic compounds can be used as the oxidizing agent.

In order to prevent a premature, unwanted reaction of the oxidation dye precursors with the oxidizing agent, the oxidation dye precursors and the oxidizing agent itself are advantageously packaged separately from one another and first brought into contact directly prior to use.

In another embodiment of the present invention, agents are therefore preferred that are characterized in that they are produced by blending at least two preparations directly prior to use, wherein the at least two preparations are provided in at least two separately packaged containers, and wherein one container comprises a dye (A) that comprises in a cosmetic carrier at least one compound a) and at least one compound b), and an additional container that comprises an oxidizing agent preparation (B), comprising at least one oxidizing agent.

The oxidizing agent preparation (B) comprises hydrogen peroxide and/or one of its solid addition products on organic or inorganic compounds, such as urea, melamine and sodium borate, as the oxidizing agent.

The quantity of oxidizing agent in the ready-to-use agent is preferably 0.5 to 12 wt %, preferably 2 to 10 wt %, particularly preferably 3 to 6 wt % (calculated as 100% conc. $H_2O_2$), each based on the ready-for-use agent.

In another preferred embodiment, the agent according to the invention is an agent for dyeing and optionally simultaneously lightening keratinic fibers which comprises 0.5 to 15 wt %, preferably 1 to 12.5 wt %, particularly preferably 1.5 to 10 wt % and in particular 2 to 6 wt % of hydrogen peroxide, each based on the total weight of the ready for use agent.

Such oxidizing agent preparations are preferably aqueous, free-flowing oxidizing agent preparations. In this regard, preferred preparations are characterized in that the free-flowing oxidizing agent preparation—based on its weight—comprises 40 to 90 wt %, preferably 50 to 85 wt %, particularly preferably 55 to 80 wt % more preferably 60 to 77.5 wt % and particularly 65 to 75 wt % water.

According to the invention, however, the oxidation dye can also be applied to the hair together with a catalyst that activates the oxidation of the dye precursors. Such catalysts are e.g. certain enzymes, iodides, quinones or metal ions.

In addition it has proven advantageous when the oxidizing agent preparations comprise at least one stabilizer or complexant. Common and in the context of the present invention preferred complexants and stabilizers are for example polyoxycarboxylic acids, polyamines, ethylenediamine tetraacetic acid (EDTA), N-hydroxyethylethylenediamine triacetic acid, diethylenetriamine pentaacetic acid (DTPA), ethylenediamine disuccinic acid (EDDS), hydroxyethylimino diacetic acid, nitridodiacetic acid-3-propionic acid, isoserine diacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HP-DDS), diaminoalkyldi-(sulfosuccinic acid) (DDS), ethylenedicysteic acid (EDC), ethylenediamine-N—N'-bis(ortho-hydroxyphenyl)acetic acid (EDDHA), N-2-hydroxyethylamine-N,N-diacetic acid, glyceryliminodiacetic acid, imino diacetic acid-N-2-hydroxy-propylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, as well as their salts and/or derivatives, geminal diphosphonic acids such as 1-hydroxyethane-1,1-diphosphonic acid (HEDP), their higher homologs with up to 8 carbon atoms as well as hydroxy- or amino group-containing derivatives thereof and 1-aminoethane-1,1-diphosphonic acid, its higher homologs with up to 8 carbon atoms as well as hydroxy- or amino group-containing derivatives, amino phosphonic acids such as ethylenediaminetetra(methylenephosphonic acid) (EDTMP), diethylenetriamine penta(methylenephosphonic acid) (DTPMP) as well as their higher homologs, or nitrilo tri(methylenephosphonic acid), phosphonopolycarboxylic acids such as 2-phosphonobutane-1,2,4-tricarboxylic acid, cyclodextrins, as well as alkali metal stannates (sodium stannate), alkali metal pyrophosphates (tetrasodium pyrophosphate, disodium pyrophosphate), alkali metal phosphates (sodium phosphate), and phosphoric acid as well as their salts.

These complexants are present, at least partially, as anions in the inventively required alkaline pH of the treatment solutions. It is immaterial whether they are introduced in the form of acids or in the form of salts. In the case that they are added as salts, alkali metal, ammonium or alkylammonium salts, in particular sodium salts, are preferred.

Inventively preferred complexants are nitrogen-containing polycarboxylic acids, especially EDTA, and phosphonates, preferably hydroxyalkane or aminoalkane phosphonates and especially 1,1-hydroxyethane-1,1-diphosphonate (HEDP) or its di- or tetrasodium salt and/or ethylenediaminetetramethylene phosphonate (EDTMP) or its hexasodium salt and/or diethylenetriaminepentamethylene phosphonate (DTPMP) or its hepta- or octasodium salt.

The dye preparation and the optional oxidizing agent preparation comprise additional auxiliaries and additives. Thus, it has proven to be inventively preferred when the dye preparation and/or the oxidizing agent preparation comprises at least one thickener. In principle there are no limitations in regard to this thickener. Both organic as well as purely inorganic thickeners can be used.

According to a first preferred embodiment, the thickener is an anionic, synthetic polymer. Carboxylate and sulfonate groups are the preferred anionic groups.

Examples of anionic monomers that can form the polymeric anionic thickener are acrylic acid, methacrylic acid, crotonic acid, itaconic acid, maleic anhydride and 2-acrylamido-2-methylpropane sulfonic acid. Here, the acidic groups may be fully or partially present as the sodium, potassium, ammonium, mono or triethanolammonium salt. Preferred monomers are maleic anhydride and in particular 2-acrylamido-2-methylpropane sulfonic acid and acrylic acid.

Preferred anionic homopolymers are uncrosslinked and crosslinked polyacrylic acids. In this regard, preferred crosslinking agents can be allyl ethers of pentaerythritol, of sucrose and of propylene. Such compounds are commercially available for example, under the trade name Carbopol®. The homopolymer of 2-acrylamido-2-methylpropane sulfonic acid, which is commercially available, for example under the trade name Rheothik® 11-80, is likewise preferred.

Within this first embodiment, it can also be preferred to use copolymers of at least one anionic monomer and at least one non-ionic monomer. Regarding the anionic monomers, reference is made to the abovementioned substances. Preferred non-ionic monomers are acrylamide, methacrylamide, acrylic acid esters, methacrylic acid esters, itaconic acid mono and diesters, vinyl pyrrolidinone, vinyl ethers and vinyl esters.

The anionic acrylic acid and/or methacrylic acid polymers or copolymers are preferably comprised in the inventive agents in an amount of 0.1 to 10 wt %, particularly preferably 1 to 5 wt %, each relative to the weight of the agent.

Preferred anionic copolymers are for example copolymers of acrylic acid, methacrylic acid or their $C_1$-$C_6$ alkyl esters, as are commercialised under the INCI name Acrylates Copolymers. A preferred commercial product for this is for example Aculyn® 33 from the Rohm & Haas company. However, copolymers of acrylic acid, methacrylic acid or their $C_1$-$C_6$ alkyl esters and of the esters of an ethylenically unsaturated acid and an alkoxylated fatty alcohol are also preferred. Suitable ethylenically unsaturated acids are particularly acrylic acid, methacrylic acid and itaconic acid; suitable alkoxylated fatty alcohols are in particular Steareth-20 or Ceteth-20. These types of copolymer are commercialized by the Rohm & Haas company under the trade name Aculyn® 22 and by the National Starch company under the trade names Structure® 2001 and Structure® 3001.

Preferred anionic copolymers are also acrylic acid-acrylamide copolymers and particularly polyacrylamide copolymers with monomers that contain sulfonic acid groups. A particularly preferred anionic copolymer consists of 70 to 55 mol % acrylamide and 30 to 45 mol % 2-acrylamido-2-methylpropane sulfonic acid, wherein the sulfonic acid group may be fully or partially present as the sodium, potassium, ammonium, mono or triethanolammonium salt. This copolymer can also be crosslinked, wherein the preferred crosslinking agents include polyolefinically unsaturated compounds such as tetraallyloxyethane, allyl sucrose, allyl pentaerythritol and methylene bisacrylamide. Such a polymer is comprised in the commercial product Sepigel® 305 and Simulgel® 600 from the SEPPIC company. The use of these compounds, which comprise a mixture of hydrocarbons ($C_{13}$-$C_{14}$ isoparaffins or isohexadecane) and a non-ionic emulsifier (Laureth-7 or Polysorbate-80) besides the polymer components, has proved to be particularly advantageous in the context of the inventive teaching.

Polymers of maleic anhydride and methyl vinyl ether, in particular those with crosslinks, are also preferred thickeners. A maleic acid-methyl vinyl ether copolymer crosslinked with 1,9-Decadien is commercially available under the trade name Stabileze® QM.

The inventive agent can preferably additionally comprise at least one anionic polymer or copolymer of acrylic acid and/or methacrylic acid. Preferred polymers of this type are:
  polymers of e.g. at least 10 wt % of lower alkyl esters of acrylic acid, 25 to 70 wt % of methacrylic acid and optionally up to 40 wt % of a further comonomer,
  mixed polymers of 50 to 75 wt % ethyl acrylate, 25 to 35 wt % acrylic acid and 0 to 25 wt % of other comonomers. Suitable dispersions of this type are commercially available, e.g. under the trade name Latekoll® D (BASF).
  copolymers of 50 to 60 wt % ethyl acrylate, 30 to 40 wt % methacrylic acid and 5 to 15 wt % acrylic acid, crosslinked with ethylene glycol dimethacrylate.

According to another embodiment, the thickener is a cationic, synthetic polymer. Preferred cationic groups are quaternary ammonium groups. In particular, those polymers, in which the quaternary ammonium groups are bonded through a $C_1$-$C_4$ hydrocarbon group to a polymer backbone formed from acrylic acid, methacrylic acid or their derivatives, have proved to be particularly suitable.

Homopolymers of the general Formula (HP-1),

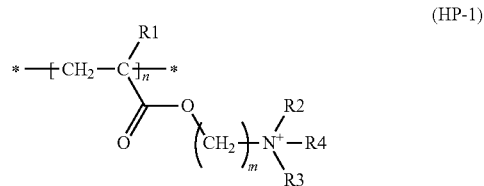

(HP-1)

in which R1=—H or —$CH_3$, R2, R3 and R4 independently of each other are selected from $C_1$-$C_4$ alkyl, -alkenyl or -hydroxyalkyl groups, m=1, 2, 3, or 4, n=a natural number and $X^-$ is a physiologically acceptable organic or inorganic anion, as well as copolymers, essentially consisting of the monomer units listed in Formula (HP-1) as well as non-ionic monomer units, are particularly preferred cationic polymeric gel formers. Regarding these polymers, those that are preferred in accordance with the invention meet at least one of the following conditions:
  R1 stands for a methyl group
  R2, R3 and R4 stand for methyl groups
  m has the value 2, Exemplary physiologically acceptable counter ions $X^-$ include halide ions, sulfate ions, phosphate ions, methosulfate ions as well as organic ions such as lactate, citrate, tartrate and acetate ions. Halide ions are preferred, particularly chloride.

A particularly suitable homopolymer is the optionally crosslinked poly(methacryloxyethyltrimethylammonium chloride) with the INCI name Polyquaternium-37. Crosslinking can be effected, when desired, with the help of olefinically polyunsaturated compounds, for example divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose. Methylene bisacrylamide is a preferred crosslinking agent.

The homopolymer is preferably employed in the form of a non-aqueous polymer dispersion that should have a polymer content of not less than 30 wt %. Such polymer dispersions are commercially available under the names Salcare® SC 95 (ca. 50% polymer content, additional components: mineral oil (INCI name: Mineral Oil) and tridecyl-polyoxypropylene polyoxyethylene ether (INCI name: PPG-1-Trideceth-6)) and Salcare® SC 96 (ca. 50% polymer content, additional components: mixture of diesters of propylene glycol with a mixture of caprylic and capric acid (INCI name: Propylene Glycol Dicaprylate/Dicaprate) and tridecyl-polyoxypropylene polyoxyethylene ether (INCI name: PPG-1-Trideceth-6)).

Copolymers with monomer units according to formula (HP-1) preferably comprise acrylamide, methacrylamide, C1-C4 alkyl esters of acrylic acid and C1-C4 alkyl esters of methacrylic acid as the non-ionic monomer units. Acrylamide is particularly preferred among these non-ionic monomers. These copolymers can also be crosslinked, as in the case of the above described homopolymers. An inventively preferred copolymer is the crosslinked acrylamide-methacryloxyethyltrimethylammonium chloride copolymer. Such copolymers, in which the monomers are present in a weight ratio of about 20:80, are commercially available as a ca. 50% conc. non-aqueous polymer dispersion named Salcare® SC 92.

In another preferred embodiment, naturally occurring thickeners are employed. Preferred thickeners of this embodiment are for example non-ionic guar gums. Both modified as well as unmodified guar gums can be inventively employed. Non-modified guar gums are sold for example under the trade name Jaguar® C (Rhone Poulenc). Inventively preferred modified guar gums comprise $C_1$-$C_6$ hydroxyalkyl groups. Hydroxymethyl, hydroxyethyl, hydroxypropyl and hydroxybutyl groups are preferred. These kinds of guar gums are known in the prior art and can be produced for example by reacting the guar gum with alkylene oxides. The degree of hydroxyalkylation which corresponds to the number of the consumed alkylene oxide molecules in relation to the number of the free hydroxy groups of the guar gum, is preferably between 0.4 and 1.2. These kinds of modified guar gum are commercially available from Rhone Poulenc under the trade names Jaguar® HP8, Jaguar® HP60, Jaguar® HP120, Jaguar® DC 293 and Jaguar® HP105.

Other suitable natural thickeners are likewise known from the prior art.

According to this embodiment, biosaccharide gums of microbial origin are further preferred, such as the scleroglucan gums or Xanthane gums, gums from vegetal exudates, such as for example gum arabicum, ghatti-gum, karaya gum, traganthe gum, carrageen gum, agar-agar, locust bean flour, pectins, alginates, starch fractions and derivatives such as amylose, amylopectin and dextrins, cellulose derivatives, such as for example methyl cellulose, carboxyalkyl celluloses and hydroxyalkyl celluloses.

Preferred hydroxyalkyl celluloses are especially the hydroxyethyl celluloses, marketed under the names Cellosize® from Amerchol and Natrosol® from Hercules. Suitable carboxyalkyl celluloses are especially the carboxymethyl celluloses, as are marketed under the names Blanose® from Aqualon, Aquasorb® and Ambergum® from Hercules and Cellgon® from Montello.

Starch and its derivatives are also preferred. Starch is a storage substance of plants which mainly occurs in bulbs and roots, in cereal seeds and in fruit and can be obtained in high yield from numerous plants. The polysaccharide, which is insoluble in cold water and forms a colloidal solution in boiling water, can be obtained for example from potatoes, manioc, batata, arrow root, maize, cereals, rice, leguminous plants such as for example peas and beans, bananas or from the core of certain types of palms (for example sago palm). Natural starches, obtained from plants, and/or chemically or physically modified starches are inventively employable. Modifications can be achieved for example by introducing different functional groups at one or more of the hydroxy groups of the starch. These are usually esters, ethers or amides of the starch with optionally substituted $C_1$-$C_{40}$ moieties. A maize starch, etherified with a 2-hydroxypropyl group, as is marketed by National Starch under the trade name Amaze®, is particularly advantageous.

However, non-ionic, fully synthetic polymers, such as for example polyvinyl alcohol or polyvinyl pyrrolidinone, can also be employed as the thickeners according to the invention. Preferred non-ionic, fully synthetic polymers are marketed by BASF under the trade name Luviskol®. In addition to their excellent thickening properties, such non-ionic polymers also confer to the resulting preparations a significant improvement in the sensorial feeling.

In the context of the invention, layered silicates (polymers, crystalline sodium disilicates) have proven to be particularly suitable as inorganic thickeners. Especially clays, especially magnesium aluminum silicates, such as for example Bentonite, particularly Smectites, such as Montmorillonite or Hectorite, which can also have been suitably modified, and synthetic layered silicates, such as the layered magnesium silicate, marketed by Süd Chemie under the trade name Optigel®, are preferred.

In order to further enhance the power of the oxidizing agent preparation, at least one optionally hydrated $SiO_2$ compound can be additionally added to the inventive preparation. According to the invention it may be preferred to use the optionally hydrated $SiO_2$ compounds in amounts of 0.05% by weight to 15% by weight, particularly preferably in amounts of 0.15% by weight to 10% by weight and quite particularly preferably in amounts of 0.2% by weight to 5% by weight, in each case based on the anhydrous preparation according to the invention. In this regard, the quantities each reflect the content of the $SiO_2$ compounds (without their water content) in the agents.

With regard to the optionally hydrated $SiO_2$ compounds, the present invention is not in principle subject to any limitations. Preference is given to silicic acids, their oligomers and polymers, and their salts. Preferred salts are the alkali metal salts, in particular the potassium and sodium salts. The sodium salts are quite particularly preferred.

The optionally hydrated $SiO_2$ compounds can exist in various forms. According to the invention, the $SiO_2$ compounds are preferably used in the form of silica gels or particularly preferably as a water-glass. These $SiO_2$ compounds may be partly in the form of an aqueous solution.

According to the invention, quite particular preference is given to water-glasses that are formed from a silicate of the formula $(SiO_2)_n(Na_2O)_m(K_2O)_p$, where n is a positive rational number and m and p, independently of one another, are a positive rational number or are 0, with the provisos that at least one of the parameters m or p is different from 0 and the ratio between n and the sum of m and p is between 1:4 and 4:1. Metasilicates are preferred in which the ratio between n and the sum of m and p is 1:2 or lower.

Besides the components described by the empirical formula, the water-glasses can also comprise, in small amounts, further additives, such as, for example, phosphates or magnesium salts.

Particularly preferred water-glasses according to the invention are marketed, inter alia, by Henkel under the names Ferrosil® 119, Natronwasserglas 40/42, Portil® A, Portil® AW and Portil® W and from Akzo under the name Britesil® C20.

The preparation (A) and/or optionally the oxidizing agent preparation (B) are preferably packaged as free-flowing preparations.

An emulsifier or a surfactant is preferably also added to the free-flowing preparations (A) and/or (B), wherein surface active substances are designated as surfactants or as emulsifiers depending on their field of application, and are selected from anionic, cationic, zwitterionic, amphoteric and non-ionic surfactants and emulsifiers. These substances are described in detail below.

Suitable anionic surfactants for the inventive preparations are all anionic surface-active materials that are suitable for use on the human body. They are characterized by a water-solubilizing anionic group, such as for example a carboxylate, sulfate, sulfonate or phosphate group and a lipophilic alkyl group containing about 8 to 30 carbon atoms. In addition, the molecule may comprise glycol or polyglycol ether groups, ester, ether and amide groups as well as hydroxy groups. Exemplary suitable anionic surfactants are, each in the form of the sodium, potassium and ammonium as well as the mono, di and trialkanolammonium salts containing 2 to 4 carbon atoms in the alkanol group, linear and branched fatty acids containing 8 to 30 carbon atoms (soaps), ether carboxylic acids of the formula RO—(CH$_2$—CH$_2$)$_x$—CH$_2$—COOH, in which R is a linear alkyl group with 8 to 30 carbon atoms and x=0 or 1 to 16, acyl sarcosides with 8 to 24 carbon atoms in the acyl group, acyl taurides with 8 to 24 carbon atoms in the acyl group, acyl isethionates with 8 to 24 carbon atoms in the acyl group, mono and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethyl groups, linear alkane sulfonates containing 8 to 24 carbon atoms, linear α-olefin sulfonates containing 8 to 24 carbon atoms, sulfonates of unsaturated fatty acids with 8 to 24 carbon atoms and 1 to 6 double bonds, methyl esters of α-sulfofatty acids with 8 to 30 carbon atoms in the fatty acid, alkyl sulfates and alkyl ether sulfates of the Formula RO(CH$_2$CH$_2$O)$_x$SO$_3$H, in which R is preferably a linear alkyl group containing 8 to 30 carbon atoms and x=0 or 1 to 12, mixtures of surface-active hydroxysulfonates, sulfated hydroxyalkyl polyethylene glycol ethers and/or hydroxyalkylene propylene glycol ethers, esters of tartaric acid and citric acid with alcohols, which represent the addition products of about 2-15 molecules of ethylene oxide and/or propylene oxide on fatty alcohols containing 8 to 22 carbon atoms, alkyl ether phosphates and/or alkenyl ether phosphates of the Formula

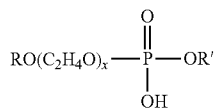

in which R preferably stands for an aliphatic, optionally unsaturated hydrocarbon residue containing 8 to 30 carbon atoms, R' for hydrogen, a (CH$_2$CH$_2$O)$_y$R residue and x and y independently of one another stand for a number from 1 to 10, sulfated fatty acid alkylene glycol esters of the Formula RC(O)O(alkO)$_n$SO$_3$H, in which R stands for a linear or branched, aliphatic, saturated and/or unsaturated alkyl residue with 6 to 22 carbon atoms, alk for CH$_2$CH$_2$, CHCH$_3$CH$_2$ and/or CH$_2$CHCH$_3$ and n for a number from 0.5 to 5, monoglyceride sulfates and monoglyceride ether sulfates.

Preferred anionic surfactants are alkyl sulfates, alkyl ether sulfates and ether carboxylic acids containing 10 to 18 carbon atoms in the alkyl group and up to 12 glycol ether groups in the molecule.

Zwitterionic surfactants are designated as those surface-active compounds that carry at least one quaternary ammonium group and at least one carboxylate, sulfonate or sulfate group in the molecule. Exemplary suitable zwitterionic surfactants are the so-called betaines such as the N-alkyl-N,N-dimethylammonium glycinates, for example the cocoalkyldimethylammonium glycinate, N-acylaminopropyl-N,N-dimethylammonium glycinates, for example the cocoacylaminopropyl-dimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethylcarboxymethyl glycinate. A preferred zwitterionic surfactant is the fatty acid amide derivative, known under the INCI name Cocamidopropyl Betaine.

Ampholytic surfactants are understood to include such surface-active compounds that apart from a C$_8$-C$_{24}$ alkyl or acyl group, comprise at least one free amino group and at least one —COOH or —SO$_3$H group in the molecule, and are able to form internal salts. Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred amphoteric surfactants are N-cocoalkylamino propionate, the cocoacylaminoethylamino propionate and the C$_{12}$-C$_{18}$ acyl sarcosine.

Furthermore, it has proven advantageous when the dye and lightening agents according to the invention comprise additional non-ionic surface active substances. Non-ionic surfactants comprise e.g. a polyol group, a polyalkylene glycol ether group or a combination of polyol and polyglycol ether groups as the hydrophilic group. Exemplary compounds of this type are addition products of 1 to 50 moles ethylene oxide and/or 0 to 5 moles propylene oxide to linear and branched fatty alcohols containing 8 to 30 carbon atoms, such as for example lauryl, myristyl, cetyl, but also stearyl, isostearyl and oleyl alcohol, to fatty acids containing 8 to 30 carbon atoms and to alkyl phenols containing 8 to 15 carbon atoms in the alkyl group, methyl or C$_2$-C$_6$ alkyl group end blocked addition products of 1 to 50 moles ethylene oxide and/or 0 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydol® LS, Dehydol® LT (Cognis), polyglycerin esters and alkoxylated polyglycerin esters, such as for example poly(3)glycerin diisostearate (commercial product: Lamefotin® TGI (Henkel)) and poly(2)glycerin polyhydroxystearate (commercial product: Dehymuls® PGPH (Henkel)).

polyol esters of fatty acids, such as, for example, the commercial product Hydagen® HSP (Cognis) or Sovermol types (Cognis), higher alkoxylated, preferably propoxylated and in particular ethoxylated mono, di and triglycerides, such as for example glycerin monolaurate+20 ethylene oxide, and glycerin monostearate+20 ethylene oxide, amine oxides, hydroxy mixed ethers, sorbitol esters of fatty acids and addition products of ethylene oxide to sorbitol esters of fatty acids such as for example the polysorbates and sorbitol monolaurate+20 moles ethylene oxide (BO), sugar esters of fatty acids and addition products of ethylene oxide to sugar esters of fatty acids, addition products of ethylene oxide to fatty acid alkanolamides and fatty amines, fatty acid N-alkylglucamides, alkylphenols and alkylphenol alkoxylates with 6 to 21, in particular 6 to 15 carbon atoms in the alkyl chain and 1 to 30 ethylene oxide and/or propylene oxide units. Preferred representatives of this class are for example nonylphenol+9 EO and octylphenol+8 EO;

alkyl polyglycosides corresponding to the general formula RO—(Z)$_x$, wherein R stands for alkyl, Z for sugar and x for the number of sugar units. The alkyl polyglycosides used according to the invention may simply comprise a defined alkyl group R. However normally, these compounds are manufactured from natural fats and oils or mineral oils. In which case, the alkyl groups R are present as mixtures corresponding to the starting compounds or to each of the compounds worked up. The alkyl polyglycosides used according to the invention comprise on average 1.1 to 5 sugar units. Alkyl polyglycosides with x-values of 1.1 to 2.0 are preferred. Alkyl glycosides with x-values of 1.1 to 1.8 are quite particularly preferred. The alkoxylated homologues of the cited alkyl polyglycosides can also be used according to the invention. These homologs can comprise on average up to 10 ethylene oxide and/or propylene oxide units per alkyl glycoside unit.

The anionic, non-ionic, zwitterionic or amphoteric surfactants are employed in quantities of 0.1-45 wt %, preferably 1-30 wt % and quite particularly preferably from 1-15 wt %, based on the total amount of the ready-to-use agent.

According to the invention, cationic surfactants of the type quaternary ammonium compounds, the esterquats and the amido amines are likewise preferred. Preferred quaternary ammonium compounds are ammonium halides, particularly chlorides and bromides, such as alkyltrimethylammonium chlorides, dialkyldimethylammonium chlorides and trialkyl-methylammonium chloride, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations Quaternium-27 and Quaternium-83. The long alkyl chains of the above-mentioned surfactants have preferably 10 to 18 carbon atoms. The quaternized protein hydrolysates illustrate further inventively usable cationic surfactants.

The alkylamido amines are normally manufactured by the amidation of natural or synthetic fatty acids and fatty acid fractions with dialkylamino amines and are characterized, in addition to a good conditioning effect, specifically by their good bio-degradability. According to the invention, a particularly suitable compound from this substance group is represented by stearamidopropyldimethylamine, commercially available under the designation Tegamid® S18.

Quaternary ester compounds, the so-called "esterquats" are likewise highly biologically degradable. Esterquats are known compounds, which both comprise at least one ester function and also at least one quaternary ammonium group as structural elements. Preferred esterquats are ester salts of fatty acids quaternized with triethanolamine, ester salts of fatty acids quaternized with diethanolalkylamines and ester salts of fatty acids quaternized with 1,2-dihydroxypropyl-dialkylamines. Such products are marketed, for example, under the trade names Stepantex®, Dehyquart® and Armocare®. The products Armocare® VGH-70, an N,N-bis (2-palmitoyloxyethyl)dimethylammonium chloride, as well as Dehyquart® F-75, Dehyquart® C-4046, Dehyquart® L80 and Dehyquart® AU 35 are examples of such esterquats.

The agents used according to the invention preferably comprise the cationic surfactants in quantities of 0.05 to 10 wt %, based on the total agent. Quantities of 0.1 to 5 wt % are particularly preferred.

In a preferred embodiment, non-ionic, zwitterionic and/or amphoteric surfactants as well as mixtures thereof can be preferred.

In a further preferred embodiment of the invention, the action of the inventive active principle can be increased by emulsifiers. Exemplary emulsifiers are addition products of 4 to 30 moles ethylene oxide and/or 0 to 5 moles propylene oxide to linear fatty alcohols containing 8 to 22 carbon atoms, to fatty acids containing 12 to 22 carbon atoms and to alkyl phenols containing 8 to 15 carbon atoms in the alkyl group, $C_{12}$-$C_{22}$ fatty acid mono and diesters of addition products of 1 to 30 mol ethylene oxide on polyols containing 3 to 6 carbon atoms, especially on glycerin, ethylene oxide- and polyglycerin-addition products on methyl glucoside fatty acid esters, fatty acid alkanolamides and fatty acid glucamides, $C_8$-$C_{22}$ alkyl mono and oligoglycosides and their ethoxylated analogs, wherein the degrees of oligomerization are 1.1 to 5, particularly 1.2 to 2.0, and glucose as the sugar component are preferred, mixtures of alkyl (oligo) glucosides and fatty alcohols, for example the commercially available product Montanov® 68, addition products of 5 to 60 mol ethylene oxide onto castor oil and hydrogenated castor oil, partial esters of polyols containing 3 to 6 carbon atoms with saturated fatty acids containing 8 to 22 carbon atoms, Sterols are understood to mean a group of steroids, which carry a hydroxyl group on carbon atom 3 of the steroid skeleton and are isolated both from animal tissue (zoosterols) and vegetal fats (phytosterols). Examples of zoosterols are cholesterol and lanosterol. Examples of suitable phytosterols are ergosterol, stigmasterol and sitosterol. Sterols, the so-called mycosterols, are also isolated from fungi and yeasts.

phospholipids, principally the glucose-phospholipids, which are obtained e.g. as lecithins or phosphatidyl cholines from e.g. egg yolk or plant seeds (e.g. soya beans), fatty acid esters of sugars and sugar alcohols, such as sorbitol, polyglycerins and polyglycerin derivatives such as for example polyglycerin poly-12-hydroxystearate (commercial product Dehymuls® PGPH).

linear and branched fatty acids with 8 to 30 carbon atoms and their Na, K, ammonium, Ca, Mg and Zn salts.

The inventive agents preferably comprise the emulsifiers in quantities of 0.1 to 25 wt %, particularly 0.5 to 15 wt %, based on the total amount of the ready-to-use agent.

Non-ionic emulsifiers or surfactants with an HLB value of 10-15 can be particularly inventively preferred. Among the cited emulsifier types the emulsifiers that comprise neither ethylene oxide nor propylene oxide in the molecule can be quite particularly preferred.

Moreover, exemplary additional active substances, adjuvants and additives, which can be comprised in the inventive agents, are:

non-ionic polymers such as for example vinyl pyrrolidinone vinyl acrylate copolymers, polyvinyl pyrrolidinone, vinyl pyrrolidinone vinyl acetate copolymers, polyethylene glycols and polysiloxanes;

silicones such as volatile or non-volatile, straight chained, branched or cyclic, crosslinked or non-crosslinked polyalkylsiloxanes (such as dimethicones or cyclomethicones), polyarylsiloxanes and/or polyalkylarylsiloxanes, in particular polysiloxanes with organofunctional groups, such as substituted or unsubstituted amines (amodimethicones), carboxyl, alkoxy and/or hydroxy groups (dimethicone copolyols), linear polysiloxane (A)-polyoxyalkylene(B) block copolymers, grafted silicon polymers with a non-silicon-containing, organic backbone or with a polysiloxane backbone, such as for example the commercial product Abil B 8832 marketed by Degussa under the INCI name Bis-PEG/PPG-20/20 Dimethicone, or mixtures thereof;

cationic polymers such as quaternized cellulose ethers, polysiloxanes with quaternary groups, dimethyldiallylammonium chloride polymers, acrylamide-dimethyldiallylammonium chloride copolymers, dimethylamino ethyl methacrylate-vinyl pyrrolidinone copolymers quaternized with diethyl sulfate, vinyl pyrrolidinone-imidazolinium-methochloride-copolymers and quaternized polyvinyl alcohol;

zwitterionic and amphoteric polymers such as for example acrylamidopropyltrimethylammonium chloride/acrylate copolymers and octylacrylamide/methyl methacrylate/tert-butylamino ethyl methacrylate/2-hydroxypropyl methacrylate copolymers, diallyldimethylammonium chlorid/acrylate copolymers, t-butylaminoethyl methacrylate N-(1,1,3,3-tetramethyl-butyl)acrylamide/acrylate(/methacrylate) copolymers, anionic polymers, such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.-butylacrylamide terpolymers, additional thickeners like agar-agar, guar gum, alginates, xanthane gum, gum arabica, karaya gum, locust bean flour, linseed gums, dextrans, cellulose derivatives, e.g. methyl cellulose, hydroxyalkyl cellulose and carboxymethyl cellulose, starch fractions and derivatives like amylose, amylopectin and dextrins, clays such as e.g. bentonite or synthetic hydrocolloids such as e.g. polyvinyl alcohol, structurants such as glucose, maleic acid and lactic acid, hair conditioning compounds like phospholipids, for example soya lecithin, egg lecithin and cephalin, as well as silicone oils, perfume oils, dimethyl isosorbitol and cyclodextrins, solvents and solubilizers such as ethanol, isopropanol, ethylene glycol, propylene glycol, glycerin and diethylene glycol, fiber structure improvers, particularly mono, di and oligosaccharides, such as, for example glucose, galactose, fructose, fruit sugar and lactose, quaternized amines, such as methyl-1-alkylamidoethyl-2-alkylimidazolinium methosulfate defoamers such as silicones, dyestuffs to color the agent, anti-dandruff active materials such as Piroctone Olamine, zinc Omadine and Climbazole, amino acids and oligopeptides, in particular arginine and/or serine, animal and/or plant based protein hydrolysates, such as for example elastin, collagen, keratin, silk and milk albumin protein hydrolysates, or almond, rice, pea, potato and wheat protein hydrolysates, as well as in the form of their fatty acid condensation products or optionally anionically or cationically modified derivatives, vegetal oils, for example macadamia nut oil, candle nut oil, palm oil, amaranth seed oil, peach stone oil, avocado oil, olive oil, cocoa oil, rape seed oil, sesame oil, jojoba oil, soja oil, peanut oil, evening primrose oil and tea tree oil light stabilizers, in particular derivatized benzophenones, cinnamic acid derivatives and triazines, substances for adjusting the pH, such as, for example, customary acids, in particular food acids and bases, active ingredients, such as panthenol, pantothenic acid, pantolactone, allantoin, pyrrolidinone carboxylic acids and salts thereof as well as bisabolol, polyphenols, particularly hydroxycinnamic acids, 6,7-dihydroxycoumarin, hydroxybenzoic acids, catechol, tannins, leucoanthocyanidines, anthocyanidines, flavanones, flavones and flavonols, Ceramides, preferably the sphingolipids such as Ceramide I, Ceramide II, Ceramide 1, Ceramide 2, Ceramide 3, Ceramide 5 and Ceramide 6, or pseudoceramides, such as in particular N—($C_8$-$C_{22}$ acyl)-($C_8$-$C_{22}$ acyl)-hydroxyproline, vitamins, provitamins and vitamin precursors, in particular those of groups A, $B_3$, $B_5$, $B_6$, C, E, F and H, plant extracts such as for example the extracts of aloe vera, angelica, aniseed, apricot, benzoin, bergamot, birch, stinging nettle, calmus, cassis, costic, marshmallow, oak bark, elemi, estragon, spruce needles, galbanum, geranium, ginseng, grapefruit, guaiacum wood oil, green tea, hamamelis, rest harrow, hops, coltsfoot, ginger root, iris, jasmin, camomile, cardamum, clover, burdock root, Scotch fir, kiwi, coconut, coriander, caraway, larch, lavender, lemon grass, lily, lime, linden blossom, litchi, mace, malva, almond, mango, rest harrow, melon, meristem, myrrh, neroli, olibanum, opoponax, orange, patchouli, petitgrain, pine, quendel, rooibos, rose, rosemary, horse chestnut, sandal wood, sage, field horsetail, common yarrow, celery, fir, thyme, juniper, vine leaves, hawthorn, wheat, lady's smock, ylang-ylang, cedar and lemon.

cholesterol, texturizers such as sugar esters, polyol esters or polyol alkyl ethers, fats and waxes such as spermaceti, beeswax, Montan wax and paraffins, fatty acid alkanolamides, swelling and penetration substances such as glycerin, propylene glycol monoethyl ether, carbonates, hydrogen carbonates, guanidines, ureas, and primary, secondary and tertiary phosphates, opacifiers such as latex, styrene/PVP copolymers and styrene/acrylamide copolymers pearlizing compositions such as ethylene glycol mono and distearate as well as PEG-3 distearate, pigments, stabilizers for hydrogen peroxide and other oxidizing agents, propellants such as propane-butane mixtures, $N_2O$, dimethyl ether, $CO_2$ and air, antioxidants.

The person skilled in the art will select these additional materials as a function of the desired properties of the agent.

With regard to further optional ingredients and their amounts used, reference is expressly made to the relevant handbooks known to the person skilled in the art, for example the monograph by K. Schräder, Grundlagen and Rezepturen der Kosmetika, 2nd edition, Hüthig Buch Verlag, Heidelberg, 1989.

The additional active substances and auxiliaries are preferably incorporated in the agents according to the invention in amounts of 0.0001 to 10 wt %, particularly 0.0005 to 5 wt %, based on the total weight of the application mixture.

Employing only hydrogen peroxide or its addition products on organic or inorganic compounds is often insufficient for strongly lightening very dark hair. Consequently, the agents according to the invention can additionally comprise still further blonding and/or bleaching agents.

If a strong lightening is desired in addition to dyeing the keratinic fibers, then it is inventively preferred to additionally mix a blonde-dyeing preparation (C) that comprises at least one bleach booster with the mixture of the oxidizing agent preparation (B) and the preparation (A), comprising at least one oxidation dye precursor according to Formula (I).

In this regard, it can be irrelevant whether a mixture of (A) and (B) is initially produced and then the blonde-dyeing preparation (C) is blended in, or whether a different sequence of blending of the individual components is utilized. It is preferred to blend the individual preparations in the shortest possible period of time and to apply the ready-to-use agent preferably promptly onto the keratinic fibers.

Consequently, another embodiment of the present application is an agent for bleaching and dyeing keratinic fibers, characterized in that it is produced prior to the application by blending at least one oxidizing agent preparation (B) that comprises at least one oxidizing agent, selected from hydrogen peroxide and its addition products on solid carriers, with at least one blond-dyeing preparation (C) that comprises at least one bleach booster, and at least one preparation (A), comprising in a cosmetic carrier at least one oxidation dye precursor according to Formula (I).

In another embodiment, it is preferred when the colorant according to the invention additionally comprises at least one inorganic peroxy compound as the blonding preparation (C). The inorganic peroxy compound is preferably selected from ammonium persulfate, alkali metal persulfates, ammonium peroxymonosulfate, alkali metal hydrogen peroxymonosulfates, alkali metal peroxydiphosphates and alkaline earth metal peroxides. Particularly preferred inorganic peroxy compounds as the bleach boosters are ammonium peroxydisulfate, potassium peroxydisulfate, sodium peroxydisulfate, potassium hydrogen peroxymonosulfate, potassium peroxydiphosphate, magnesium peroxide and barium peroxide, especially ammonium peroxydisulfate, potassium peroxydisulfate and sodium peroxydisulfate.

The inorganic peroxy compounds are preferably comprised in an amount of 0.1 to 25 wt %, particularly in an amount of 0.5 to 15 wt %, based on the total weight of the ready for use agent.

The persulfate salts or peroxydisulfate salts are generally added in the form of an optionally de-dusted powder or in the form of a compressed molded body.

However, it can be inventively advantageous for the agent to be exempt from inorganic peroxy compounds. Consequently, the agents according to the invention can, however, comprise an additional bleach booster, instead of and/or in addition to the solid peroxy compounds.

In the context of this invention, additional bleach boosters can be added such as compounds that under perhydrolysis conditions afford aliphatic peroxycarboxylic acids, for example polyacylated alkylenediamines—especially tetraacetyl ethylenediamine (TAED)—and/or substituted perbenzoic acid, carbonic acid derivatives, for example ammonium hydrogen carbonate, ammonium carbonate, sodium hydrogen carbonate, sodium carbonate, potassium hydrogen carbonate, potassium carbonate and calcium carbonate, alkyl carbonates and alkyl carbamates as well as silyl carbonates and silyl carbamates.

The bleach boosters employed in addition to, or instead of, peroxy compounds are comprised in the cosmetic agents according to the invention preferably in amounts of 0.05 to 10% by weight, in particular in amounts of 0.2 to 5% by weight, each based on the total weight of the ready-for-use agent.

Although in principle there is no limitation in regard to the formulation of the blonding preparation (C), it has proved to be inventively preferred when the preparation (C) is an anhydrous formulation.

In the context of the present invention, anhydrous means a water content, based on the preparation (C), of less than 5 wt %, especially less than 2 wt %. Blonding preparations that comprise less than 0.1 wt % water can be inventively quite particularly preferred. The preparation (C) is preferably formulated as a powder or an anhydrous paste.

In another preferred embodiment, the agent in the preparation (C) can comprise at least one cationic pyridinium derivative as the bleach booster. Inventive agents are particularly preferred which comprise a compound from 2-acetyl-1-methylpyridinium p-toluene sulfonate and/or 4-acetyl-1-methylpyridinium p-toluene sulfonate and/or N-methyl-3,4-dihydroisoquinolinium p-toluene sulfonate as the cationic pyridinium derivative.

An inventively preferred embodiment of the present invention consists in that the ready-to-use agent exhibits a pH between 7 and 11, particularly between 8 and 10.5, particularly preferably between 8.5 and 10.0.

The pH is usually adjusted with pH adjustors. The person skilled in cosmetics commonly uses established acidifiers and alkalizers to adjust the pH. The alkalizers that can be used for adjusting the pH are typically selected from inorganic salts, especially from the alkali metals and alkaline earth metals, from organic alkalizers, especially amines, basic amino acids and alkanolamines, and ammonia. Inventively preferred acidifiers are food acids, such as for example citric acid, acetic acid, malic acid or tartaric acid, as well as diluted mineral acids.

In the context of the present invention, the pH values refer to those measured at a temperature of 22° C.

Inventively useable organic alkalizers are preferably selected from alkanolamines from primary, secondary or tertiary amines containing a $C_2$-$C_6$ alkyl parent substance that carries at least one hydroxy group. Particularly preferred alkanolamines are selected from the group 2-aminoethan-1-ol (monoethanolamine), 2-amino-2-methylpropan-1-ol, 2-amino-2-methyl-propane-1,3-diol and triethanolamine.

However, in the context of the experiments for the present invention, it was found furthermore that inventively preferred agents are characterized in that they additionally comprise an inorganic alkalizer. The inorganic alkalizer according to the invention is preferably selected from the group consisting of sodium hydroxide, potassium hydroxide, calcium hydroxide, barium hydroxide, sodium phosphate, potassium phosphate, sodium silicate, potassium silicate, sodium carbonate and potassium carbonate. Sodium hydroxide and/or potassium hydroxide are quite particularly preferred.

In the context of the invention, the basic amino acids that can be employed as an inventive alkalizer are preferably selected from the group consisting of L-arginine, D-arginine, D,L-arginine, L-lysine, D-lysine, D,L-lysine, particularly preferably L-arginine, D-arginine, D,L-arginine.

Finally, ammonia is another preferred alkalizer.

The alkalizers are preferably comprised in amounts of 0.05 to 10 wt %, particularly 0.5 to 5 wt %, each based on the total weight of the ready-to-use agent.

As already mentioned, the agents according to the invention can also be produced from two or more separately packaged preparations immediately prior to use. This lends itself in particular to the separation of incompatible ingredients in order to avoid premature reaction. A separation into multi-component systems is particularly appropriate in cases where incompatibilities of the ingredients are to be expected or feared. In systems of this type, the ready-to-use agent is produced by the user by blending the components immediately prior to use. A dyeing and/or lightening agent, in which the oxidation dye precursors are initially separated from the oxidizing agent preparation, is preferred in this regard.

A further preferred presentation form of the agent according to the invention is a kit-of-parts that in separately packaged containers comprises in a container A at least one preparation (A), comprising in a cosmetic carrier at least one oxidation dye precursor according to the Formula (I), and in a container B at least one oxidizing agent preparation (B), comprising in a cosmetic carrier at least one oxidizing agent.

If a particularly strong lightening effect is desired, then a further preferred presentation form of the agent according to the invention is a kit-of-parts that in separately packaged containers comprises in a container A at least one preparation (A), comprising in a cosmetic carrier at least one compound a) and at least one compound b), in a container B at least one oxidizing agent preparation (B), comprising at least one oxidizing agent, and in a container C at least one blonding preparation (C), comprising at least one bleach booster.

The multi-component kit-of-parts preferably additionally comprises an instruction manual. Moreover, it can be preferred that an application aid, such as for example a comb or a brush, and/or a personal protection kit, such as for example disposable gloves, is supplied with the kit.

With reference to further preferred embodiments of the multi-component kit-of-parts, the statement made concerning the agents according to the invention applies mutatis mutandis.

The actual hair dye is advantageously produced immediately prior to the application by mixing the preparations (A) with (B) as well as optionally (C). The application temperatures can be in a range between 15 and 40° C. After a contact time of 5 to 45 minutes, the hair dye is removed from the hair by rinsing. There is no need to wash the hair with a shampoo afterwards if a strong surfactant-containing carrier, e.g. a color enhancing shampoo, was used.

During the contact time of the agent with the fibers, it can be advantageous to support the dyeing process by supplying heat. The supply of heat can be from a heat source, such as e.g. warm air from a stream of warm air, as also, especially for a hair coloration on living subjects, from the body temperature of the subject. For the latter alternative, the areas being dyed are normally covered with a cap. In particular, the temperature during the contact time is between 10° C. and 45° C., particularly between 20° C. and 40° C. The inventive dyes furnish intensive colorations already at physiologically compatible temperatures of below 45° C. In consequence, they are particularly suitable for dyeing human hair.

A further subject matter of the present invention is the use of an agent according to the invention in dyes for human hair so as to improve the gray coverage, the leveling, the color intensity, the durability and/or the vividness of the dyeing results.

With reference to further preferred embodiments of the use according to the invention, the statement made concerning the agents according to the invention applies mutatis mutandis.

EXAMPLES

1) Synthesis Examples a) 6-Methoxy-2,4,5-pyrimidinetriamine, dihydrochloride (i) Synthesis of 6-Methoxy-2,4-diaminopyrimidine

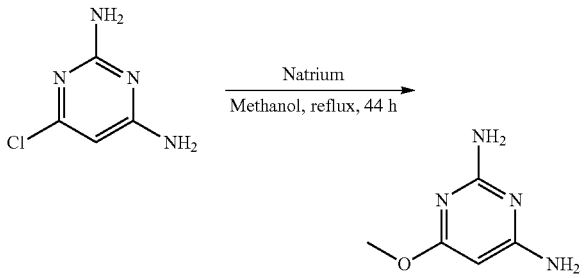

To a solution of 9.2 g (0.40 mol) sodium in 320 ml methanol were added 28.9 g (0.20 mol) 2,4-diamino-6-chloropyrimidine. The mixture was heated under reflux with stirring for 44 h. After the reaction was ended the precipitated NaCl was separated off and the solution was concentrated to dryness. The residue in 300 ml ethanol was heated to boiling and filtered hot. The product precipitated out of the filtrate on standing overnight. Recrystallization of the mother liquor likewise afforded product. After drying, 6-methoxy-2,4-diaminopyrimidine was obtained as a white solid (58.8 g, 84%).

m.pt.: 166-169° C.

$^1$H-NMR (300 MHz, $d_6$-DMSO): δ=3.18 (s, 3H, 6-OMe), 5.06 (s, 1H, 5-H), 5.94 (s, 2H, $NH_2$), 6.05 (s, 2H, $NH_2$).

$^{13}$C-NMR (125 MHz, $d_6$-DMSO): δ=52.8 (6-OMe), 76.1 (5-C), 163.3 (2-C), 166.3 (4-C), 170.8 (6-C).

(ii) Synthesis of 5-Nitroso-2,4-diamino-6-methoxypyrimidine

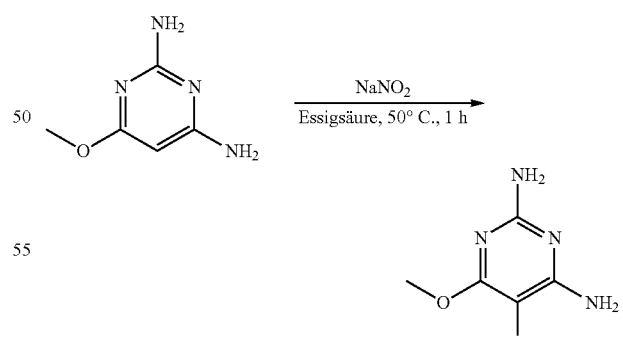

(Essigsäure=acetic acid)

To a stirred solution of 7.0 g (0.05 mol) 6-methoxy-2,4-diaminopyrimidine in 100 ml acetic acid (10% conc. in water) at 50-60° C. was added dropwise over a period of 30 min a solution of 4.55 g (0.07 mol) sodium nitrite in 20 ml water. The solution was stirred at this temperature for a further 30 min and then stirred at room temperature overnight. The filtrate was filtered off with suction, washed with water and dried. 5-Nitroso-2,4-diamino-6-methoxypyrimidine (7.80 g, 92%) was obtained as a violet solid.

m.pt.: 250° C. (dec.)

$^1$H-NMR (300 MHz, d$_6$-DMSO): δ=4.04 (s, 3H, 6-OMe), 7.79 (s, 1H, NH$_2$), 7.85 (s, 1H, NH$_2$), 8.01 (s, 1H, NH$_2$), 10.10 (s, 1H, NH$_2$).

$^{13}$C-NMR (125 MHz, d$_6$-DMSO): δ=54.5 (6-OMe), 140.0 (5-C), 151.2 (2-C), 163.8 (4-C), 171.4 (6-C).

(iii) Synthesis of 6-Methoxy-2,4,5-pyrimidinetriamine, dihydrochloride

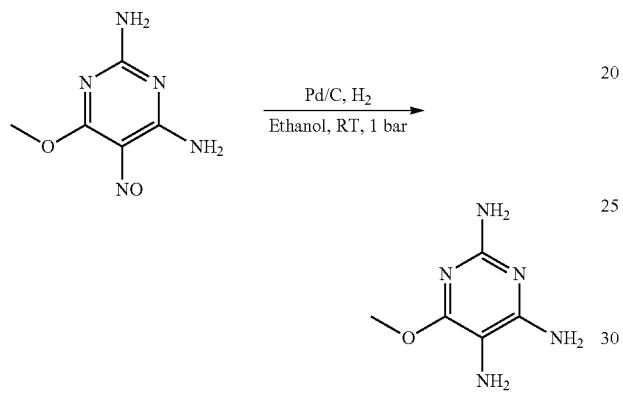

To a solution of 7.60 g (0.045 mol) 5-nitroso-2,4-diamino-6-methoxypyrimidine from step 1.2 in 400 ml ethanol was added 1.5 g (0.04 mol %) palladium on charcoal (5%). The mixture was shaken at room temperature for 16 h under an atmosphere of hydrogen at 1 bar. The reaction mixture was then poured into 80 ml dilute hydrochloric acid (0.23 mol), the catalyst was filtered off and the filtrate was concentrated almost to dryness. The precipitated crystals were filtered off with suction and washed with tert-butyl methyl ether. 6-Methoxy-2,4,5-pyrimidinetriamine dihydrochloride (8.10 g, 79%) was obtained as light yellow crystals.

m.pt.: ca. 170° C. (dec.)

$^1$H-NMR (300 MHz, d$_6$-DMSO): δ=3.91 (s, 3H, 6-OMe), 7.30 (s, 2H, NH$_2$), 7.46 (s, 2H, NH$_2$), 7.57 (s, 2H, NH$_2$).

$^{13}$C-NMR (125 MHz, d$_6$-DMSO): δ=55.3 (6-OMe), 84.9 (5-C), 151.3 (2-C), 153.9 (4-C), 164.9 (6-C).

b) 6-(2-Methylpropoxy)-2,4,5-pyrimidinetriamine, dihydrochloride (i) Synthesis of 6-(2-Methylpropoxy)-2,4-diaminopyrimidine

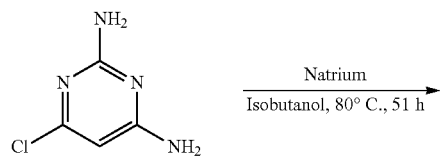

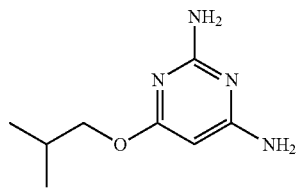

To a solution of 6.9 g (0.30 mol) sodium in 185 ml isobutyl alcohol were added 43.4 g (0.30 mol) 2,4-diamino-6-chloropyrimidine. The mixture was heated under reflux with stirring for 10 h. The reaction mixture was then stirred at 80° C. for a further 36 h. After the reaction was ended the precipitated NaCl was separated off and the solution was concentrated to dryness. The residue was repeatedly taken up in ethanol and again concentrated in order to remove residual isobutyl alcohol. After drying, 6-(2-methylpropoxy)-2,4-diaminopyrimidine (41.3 g, 75%) was obtained as a yellow oil.

$^1$H-NMR (300 MHz, d$_6$-DMSO): δ=1.49 (d, 6H, 2'-Me), 2.50 (sept, 1H, 2'-H), 4.45 (d, 2H, V—H$_2$), 5.71 (s, 1H, 5-H), 6.18 (s, 2H, NH$_2$), 6.76 (s, 2H, NH$_2$).

$^{13}$C-NMR (125 MHz, d$_6$-DMSO): δ=19.2 (2'-Me), 27.8 (2'-C), 71.3 (1'-C), 76.4 (5-C), 163.1 (2-C), 166.1 (4-C), 170.7 (6-C).

(ii) Synthesis of 5-Nitroso-2,4-diamino-6-(2-methylpropoxy)pyrimidine

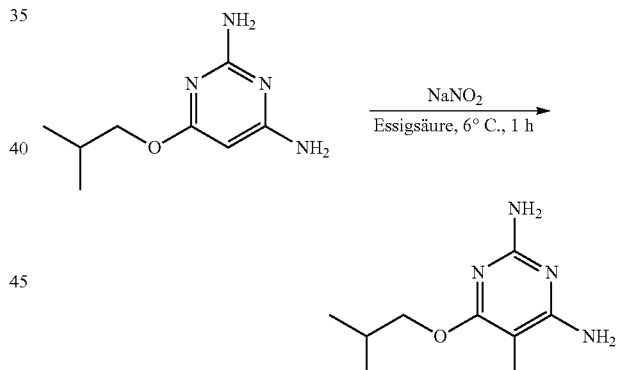

(Essigsäure=acetic acid)

To a stirred solution of 18.2 g (0.100 mol) 6-(2-methylpropoxy)-2,4-diaminopyrimidine in 100 ml acetic acid (10% conc. in water) at 6° C. was added dropwise over 1 h a solution of 9.11 g (0.132 mol) sodium nitrite in 40 ml water, whereupon the temperature was allowed to increase to 32° C. Stirring was then continued for a further 2 h at room temperature. The resulting precipitate was filtered off with suction, washed with water and dried. 5-Nitroso-2,4-diamino-6-(2-methylpropoxy)-pyrimidine (18.3 g, 81%) was obtained as a violet solid.

m.pt.: 201-212° C. (dec.)

$^1$H-NMR (300 MHz, d$_6$-DMSO): δ=0.90 (s, 6H, 2×2'-Me), 2.05 (m, 1H, 2'-H), 4.19 (s, 2H, 1'-H$_2$), 7.71 (s, 1H, NH$_2$), 7.78 (s, 1H, NH$_2$), 7.95 (s, 1H, NH$_2$), 10.05 (s, 1H, NH$_2$).

$^{13}$C-NMR (125 MHz, d$_6$-DMSO): δ=19.0 (2'-Me), 27.5 (2'-C), 72.7 (1'-C), 139.6 (5-C), 150.9 (2-C), 163.6 (4-C), 170.9 (6-C).

(iii) Synthesis of 6-(2-Methylpropoxy)-2,4,5-pyrimidinetriamine, dihydrochloride

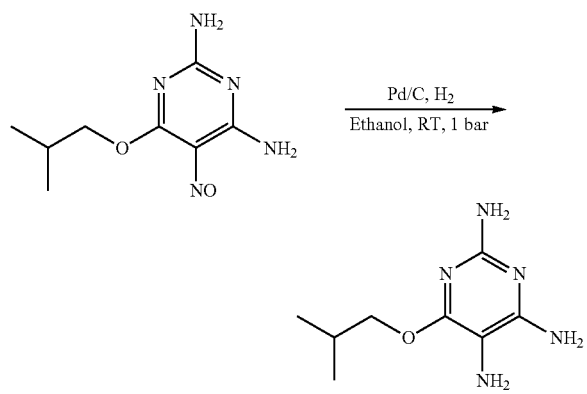

To a solution of 16.9 g (0.08 mol) 5-nitroso-2,4-diamino-6-(2-methylpropoxy)pyrimidine from step 2.2 in 400 ml ethanol was added 1.5 g (0.04 mol %) palladium on charcoal (5%). The mixture was shaken at room temperature for 16 h under an atmosphere of hydrogen at 1 bar. The reaction mixture was then poured into 105 ml dilute hydrochloric acid (0.30 mol), the catalyst was filtered off and the filtrate was concentrated almost to dryness. The precipitated crystals were filtered off with suction and washed with tert-butyl methyl ether. 6-(2-Methylpropoxy)-2,4,5-pyrimidinetriamine dihydrochloride (14.6 g, 68%) was obtained as light yellow crystals.

m.pt.: 164° C. (dec.)

$^1$H-NMR (300 MHz, D$_2$O): δ=0.96 (s, 3H, 2'-Me), 0.97 (s, 3H, 2'-Me), 2.11 (sept, 1H, 2'-H), 4.28 (d, 2H, 1'-H$_2$).

$^{13}$C-NMR (125 MHz, D$_2$O): δ=21.0 (2'-Me), 30.2 (2'-C), 78.2 (1'-C), 87.0 (5-C), 153.6 (2-C), 157.0 (4-C), 168.6 (6-C).

c) 6-(3-Methylbutoxy)pyrimidine-2,4,5-triamine, dihydrochloride

(i) Synthesis of 6-(3-Methylbutoxy)pyrimidine-2,4-diamine

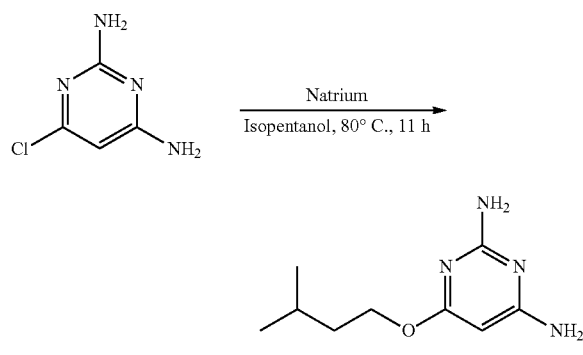

To a solution of 6.9 g (0.30 mol) sodium in 200 ml isopentyl alcohol were added 43.4 g (0.30 mol) 2,4-diamino-6-chloropyrimidine. The mixture was heated under reflux with stirring for 11 h. The reaction mixture was then stirred at 80° C. for a further 36 h. After the reaction was ended the precipitated NaCl was separated off and the solution was concentrated to dryness. The residue was repeatedly taken up in ethanol and again concentrated in order to remove residual isopentyl alcohol. After drying, 6-(3-Methylbutoxy)-2,4-diaminopyrimidine (51.8 g, 88%) was obtained as a yellow oil.

$^1$H-NMR (300 MHz, d$_6$-DMSO): δ=0.92 (d, 6H, 2×3'-Me), 1.53 (dt, 2H, 2'-H$_2$), 1.71 (sept, 1H, 3'-H), 4.12 (t, 2H, 1'-H$_2$), 5.05 (s, 1H, 5-H), 5.90 (s, 2H, NH$_2$), 6.05 (s, 2H, NH$_2$).

$^{13}$C-NMR (125 MHz, d$_6$-DMSO): d=19.0 (2'-Me), 27.5 (2'-C), 72.7 (1'-C), 139.6 (5-C), 150.9 (2-C), 163.6 (4-C), 170.9 (6-C).

(ii) Synthesis of 5-Nitroso-2,4-diamino-6-(2-methylbutoxy)pyrimidine

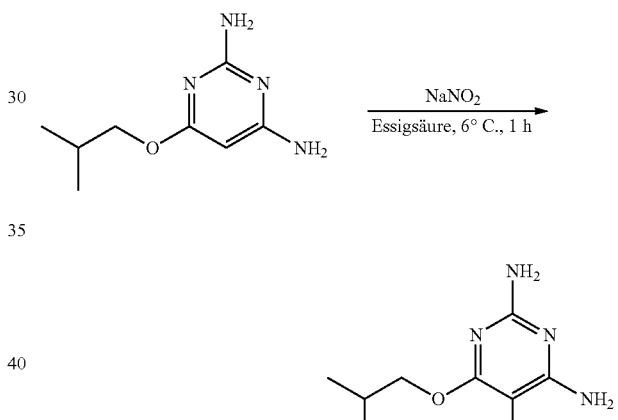

(Essigsäure=acetic acid)

To a stirred solution of 51.0 g (0.26 mol) 6-(3-methylbutoxy)-2,4-diaminopyrimidine in 520 ml acetic acid (10% conc. in water) at 55-60° C. was added dropwise over a period of 25 min a solution of 23.5 g (0.34 mol) sodium nitrite in 105 ml water. Stirring was then continued for a further 1 h at 50-55° C. and overnight at room temperature. The resulting precipitate was filtered off with suction, washed with water and dried. The crude product was recrystallized from a 1:1 mixture of water/ethanol to yield 5-nitroso-2,4-diamino-6-(2-methylbutoxy)pyrimidine (19.0 g, 32%) as a violet solid.

m.pt.: 221-223° C.

$^1$H-NMR (300 MHz, d$_6$-DMSO): δ=0.92 (s, 6H, 2×3'-Me), 1.67 (m, 1H, 2'-H$_2$), 1.76 (m, 1H, 3'-H), 4.51 (s, 2H, 1'-H$_2$), 7.75 (s, 1H, NH$_2$), 7.79 (s, 1H, NH$_2$), 7.97 (s, 1H, NH$_2$), 10.11 (s, 1H, NH$_2$).

$^{13}$C-NMR (125 MHz, d$_6$-DMSO): δ=22.7 (3'-Me), 25.0 (2'-C), 37.3 (3'-C), 65.6 (1'-C), 139.9 (5-C), 151.2 (2-C), 163.9 (4-C), 171.1 (6-C).

(iii) Synthesis of 6-(2-Methylbutoxy)-2,4,5-pyrimidinetriamine, dihydrochloride

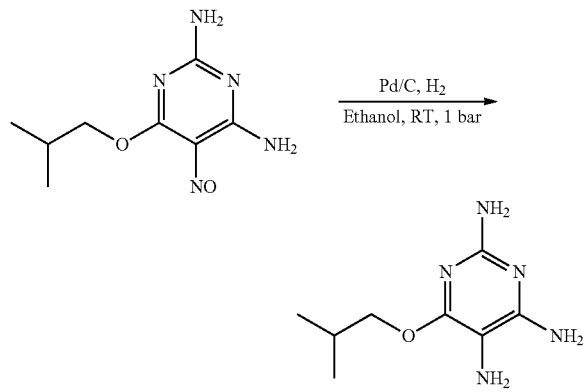

To a solution of 19.0 g (0.084 mol) 5-nitroso-2,4-diamino-6-(2-methylbutoxy)pyrimidine from step 3.2 in 400 ml ethanol was added 4.0 g (0.04 mol %) palladium on charcoal (5%). The mixture was shaken at room temperature for 18 h under an atmosphere of hydrogen at 1 bar. The reaction mixture was then poured into 150 ml dilute hydrochloric acid (0.30 mol), the catalyst was filtered off and the filtrate was concentrated almost to dryness. The precipitated crystals were filtered off with suction and washed with tert-butyl methyl ether. 6-(2-Methylbutoxy)-2,4,5-pyrimidinetriamine dihydrochloride (19.5 g, 81%) was obtained as light yellow crystals.

m.pt.: 181° C. (dec.)

$^1$H-NMR (300 MHz, $d_6$-DMSO): δ=0.87 (s, 3H, 6-OMe), 1.58 (m, 2H, 2'-$H_2$), 1.76 (m, 1H, 3'-H), 4.36 (t, 2H, 1'-$H_2$).

$^{13}$C-NMR (125 MHz, $d_6$-DMSO): δ=22.9 (3'-Me), 24.6 (3'-C), 41.0 (2'-C), 59.2 (1'-C), 85.2 (5-C), 151.5 (2-C), 154.1 (4-C), 164.9 (6-C).

2) Dyeing

Preparation of the Colorant Creams

A colorant cream was prepared with the following composition:

| | | |
|---|---|---|
| Hydrenol ® D[1] | 8.5 | wt % |
| Lorol ® tech.[2] | 2.0 | wt % |
| Texapon ® NSO[3] | 20.0 | wt % |
| Dehyton ® K[4] | 12.5 | wt % |
| Eumulgin ® B2[5] | 0.75 | wt % |
| sodium sulfite | 1.0 | wt % |
| ammonium sulfate | 1.0 | wt % |
| Developer component | 3 | mmol |
| Coupler component | 3 | mmol |
| water | ad 100 | |

[1]$C_{16-18}$ Fatty alcohol (INCI name: Cetearyl alcohol) (Cognis)
[2]$C_{12-18}$ Fatty alcohol (INCI name: Coconut Alcohol (Cognis)
[3]Lauryl ether sulfate, sodium salt (ca. 27.5% active substance; INCI-name: Sodium Laureth Sulfate) (Cognis)
[4]NN-Dimethyl-N-($C_8$-$C_{18}$-cocoamidopropyl) ammonium acetobetaine (ca. 30% active substance; INCI-name: Aqua (Water), Cocamidopropyl Betaine) (Cognis)
[5]Cetylstearyl alcohol with ca. 20 EO-units (INCI name: Ceteareth-20) (Cognis)

Hydrenol D and Lorol techn. were melted together with Texapon NSO, Dehyton K and Eumulgin B2 at 80° C. The melt was then emulsified with sodium sulfite and ammonium sulfite dissolved in part of the water. The developer according to the invention was dissolved with heating in another part of the cited amount of water and added with stirring. The coupler was likewise dissolved in a part of the cited amount of water and added with stirring. Water was then added to make up 100% and the formulation was stirred without heating.

The resulting coloration cream was blended in the ratio 1:1 with the following developer dispersion with a hydrogen peroxide content of 6%.

| | |
|---|---|
| Dipicolinic acid | 0.1 wt % |
| Sodium pyrophosphate | 0.03 wt % |
| Turpinal ® SL[6] | 1.50 wt % |
| Texapon ® N28[7] | 2.00 wt % |
| Acrysol ® 22[8] | 0.60 wt % |
| Hydrogen peroxide, 50% conc. | 6.00 wt % |
| Sodium hydroxide, 45% conc. | 0.80 wt % |
| Water | ad 100 |

[6]1-Hydroxyethane-1,1-diphosphonic acid (ca. 58-61% active substance content; INCI-name: Etidronic Acid, Aqua (Water)) (Solutia)
[7]Lauryl ether sulfate sodium salt (min. 26.5% active substance content; INCI name: Sodium Laureth Sulfate) (Cognis)
[8]Acrylpolymer (ca. 29.5-30.5% solids in water; INCI name: Acrylates/Steareth-20 Methacrylate Copolymer)

In the dyeing method, 4 times the amount of the ready-for-use mixture was applied to each strand of 80% gray hair (Kerling). After a contact time of 30 minutes at 32° C., the strands were rinsed off and washed out with a typical hair shampoo. After drying, the coloration of the strands was determined visually under the daylight lamp. The coloration results are summarized in the following Table.

a) Colorations with 6-Methoxy-2,4,5-pyrimidinetriamine, dihydrochloride

| Example | Coupler component | Obtained nuance/ color intensity |
|---|---|---|
| 1 | Resorcinol | raspberry red/+++ |
| 2 | 3-Amino-2-methylamino-6-methoxypyridine | blue gray/+++ |
| 3 | 5-Amino-2-methylphenol | gray magenta/++ |
| 4 | 3-Amino-2-hydroxypyridine | sun-tanned/+ |
| 5 | 1,3-Bis(2,4-diaminophenoxy)propane | deep violet/+++ |
| 6 | 2,7-Dihydroxynaphthalene | gray red/++ |
| 7 | 2-Methylresorcinol | blood red/+++ |

+++ high intensity
++ medium intensity
+ weak intensity b) Colorations with 6-(2-Methylpropoxy)-2,4,5-pyrimidinetriamine, dihydrochloride

| Example | Coupler component | Obtained nuance/ color intensity |
|---|---|---|
| 1 | Resorcinol | brown red/+++ |
| 2 | 3-Amino-2-methylamino-6-methoxypyridine | nickel green/+++ |
| 3 | 5-Amino-2-methylphenol | gray ruby/++ |
| 4 | 3-Amino-2-hydroxypyridine | red/+ |
| 5 | 1,3-Bis(2,4-diaminophenoxy)propane | deep blue/+++ |
| 6 | 2,7-Dihydroxynaphthalene | matt red/+ |
| 7 | 2-Methylresorcinol | brown red/+++ |

+++ high intensity
++ medium intensity
+ weak intensity c) Colorations with
6-(2-Methylpropoxy)-2,4,5-pyrimidinetriamine,
dihydrochloride

| Example | Coupler component | Obtained nuance/ color intensity |
|---|---|---|
| 1 | Resorcinol | red brown/+++ |
| 2 | 3-Amino-2-methylamino-6-methoxypyridine | fir green/+++ |
| 3 | 5-Amino-2-methylphenol | gray magenta/++ |
| 4 | 3-Amino-2-hydroxypyridine | light brown/+ |
| 5 | 1,3-Bis(2,4-diaminophenoxy)propane | stormy blue/+++ |
| 6 | 2,7-Dihydroxynaphthalene | matt red/+ |
| 7 | 2-Methylresorcinol | blood red/+++ |

+++ high intensity
++ medium intensity
+ weak intensity

The colorations produced many different red nuances that exhibit excellent fastness characteristics.

The red tints in particular were found to exhibit an excellent wash fastness.

A particularly good uniformity could be observed for the colorations with 2,7-dihydroxynaphthalene.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:
1. An agent for dyeing keratinic fibers, characterized in that said agent comprises in a cosmetic carrier
a) at least one compound of Formula (I) and/or a physiologically acceptable salt of said compound,

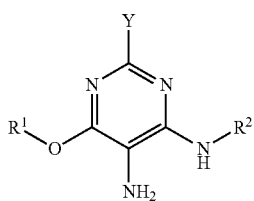

(I)

in which
$R^1$ stands for a C1-$C_4$ alkyl group,
$R^2$ stands for a hydrogen atom, a $C_1$-$C_8$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group, a $C_1$-$C_6$ alkylamino group, a di-$C_1$-$C_6$ alkylamino group a $C_1$-$C_6$ polyalkoxy group, a $C_1$-$C_6$ alkylamido-($C_1$-$C_6$) alkyl group, wherein the amide function can be substituted with one or two X groups, or stands for an aryl group,
Y stands for an $NH_2$ group or an OH group, b) at least one coupler component, selected from the group consisting of 3-amino-2-methylamino-6-methoxypyridine, 3-amino-6-methylphenol, 3-amino-2-hydroxypyridine, 1,3-bis-(2,4-diaminophenoxy)propane, 2,7-dihydroxynaphthalene, 2-methylresorcinol, 2,5-dimethylresorcinol, 4-chlororesorcinol, 3-aminophenol, 2-amino-3-hydroxypyridine, 2-chloro-6-methyl-3-aminophenol, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 1-methoxy-2-amino-4-beta-hydroxyethylaminobenzene, 2,4-diaminophenoxyethanol, 5-amino-4-chloro-o-cresol, 2,4-dichloro-m-aminophenol, 2,6-dihydroxy-3,4-dimethylpyridine and a physiologically acceptable salt of these compounds
wherein at least one compound of Formula (I) and/or a physiologically acceptable salt of said compound comprises 6-(2-methylpropoxy)-2,4,5-pyrimidinetriamine or a physiologically acceptable salt thereof and the at least one coupler includes one or more compounds selected from the group consisting of 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxyethylaminobenzene and a physiologically acceptable salt of these compounds; or
wherein at least one compound of Formula (I) and/or a physiologically acceptable salt of said compound comprises 6-(3-methylbutoxy)-2,4,5-pyrimidinetriamine or a physiologically acceptable salt thereof and the at least one coupler includes one or more compounds selected from the group consisting of 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxyethylaminobenzene, and a physiologically acceptable salt of said compounds; or
wherein at least one compound of Formula (I) and/or a physiologically acceptable salt of said compound comprises 6-methoxy-4-N-methyl-pyrimidine-2,4-diamine or a physiologically acceptable salt thereof and the at least one coupler includes one or more compounds selected from the group consisting of: 3-amino-2-methylamino-6-methoxypyridine, 3-amino-2-hydroxypyridine, 1,3-bis-(2,4-diaminophenoxy)propane, 2,7-dihydroxynaphthalene, 2-methylresorcinol, 1-methoxy-2-amino-4-β-hydroxyethylaminobenzene, and a physiologically acceptable salt of said compounds.

2. The agent according to claim 1, wherein the compounds of the Formula (I) comprises, by weight, 0.001 to 5.0 wt % of the agent.

3. The agent according to claim 1, wherein the compounds of the Formula (I) comprises, by weight, 0.025 to 2.5 wt % of the agent.

4. The agent according to claim 1, wherein the compounds of the Formula (I) comprises, by weight, 0.05 to 2.0 wt % of the agent.

5. The agent according to claim 1, wherein the compounds of the Formula (I) comprises, by weight, 0.1 to 1.5 wt % of the agent.

6. The agent according to claim 1, wherein the at least one coupler component b) comprises, by weight, 0.001 to 5.0 wt % of the agent.

7. The agent according to claim 1, wherein the at least one coupler component b) comprises, by weight, 0.025 to 2.5 wt % of the agent.

8. The agent according to claim 1, wherein the at least one coupler component b) comprises, by weight, 0.05 to 2.0 wt % of the agent.

9. The agent for dyeing according to claim 1, wherein the agent further comprises 0.5 to 15 wt % of hydrogen peroxide, based on the total weight of the agent.

* * * * *